United States Patent
Shiina

(10) Patent No.: US 8,696,573 B2
(45) Date of Patent: Apr. 15, 2014

(54) ULTRASONOGRAPHIC DIAGNOSTIC SYSTEM AND ULTRASONIC DIAGNOSTIC DEVICE

(75) Inventor: Tsuyoshi Shiina, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 277 days.

(21) Appl. No.: 13/128,245

(22) PCT Filed: Nov. 6, 2009

(86) PCT No.: PCT/JP2009/068995
§ 371 (c)(1),
(2), (4) Date: Jul. 15, 2011

(87) PCT Pub. No.: WO2010/053156
PCT Pub. Date: May 14, 2010

(65) Prior Publication Data
US 2011/0270088 A1    Nov. 3, 2011

(30) Foreign Application Priority Data
Nov. 10, 2008    (JP) ................................ 2008-288239

(51) Int. Cl.
*A61B 8/00* (2006.01)
*A61B 8/14* (2006.01)

(52) U.S. Cl.
USPC ............................ 600/437; 600/443; 600/453

(58) Field of Classification Search
None
See application file for complete search history.

(56) References Cited

U.S. PATENT DOCUMENTS

| 5,322,068 | A | * | 6/1994 | Thiele et al. ................. 600/447 |
| 6,148,224 | A | | 11/2000 | Jensen |
| 6,859,076 | B2 | | 2/2005 | Fujiwara |
| 2004/0034304 | A1 | | 2/2004 | Sumi |
| 2006/0052696 | A1 | | 3/2006 | Shiina et al. |
| 2007/0244390 | A1 | | 10/2007 | Matsumura |

FOREIGN PATENT DOCUMENTS

| JP | 2001 503853 | 3/2001 |
| JP | 2003 180686 | 7/2003 |
| JP | 2004 57653 | 2/2004 |
| JP | 2008 136880 | 6/2008 |
| WO | 2005 122907 | 12/2005 |

OTHER PUBLICATIONS

Fox, M. D., "Multiple Crossed-Beam Ultrasound Doppler Velocimetry", IEEE Transactions on Sonics and Ultrasonics, vol. 25, No. 5, pp. 281-286, (Sep. 1978).

(Continued)

*Primary Examiner* — Long V. Le
*Assistant Examiner* — Bradley Impink
(74) *Attorney, Agent, or Firm* — Fitzpatrick, Cella, Harper & Scinto

(57) ABSTRACT

An ultrasonic probe is constituted by ultrasonic transducer elements arranged in a direction. A beam forming unit forms acoustic field sensitivity modulated in a direction substantially orthogonal to scan lines in a subject by focusing an ultrasonic wave on a sequence of sampling points existing along the scan lines, and applying delay and apodization on a transmission/reception signal of each of the ultrasonic transducer elements. A detecting unit detects displacements at each sampling point in a direction tangential to the scan lines and in a direction tangential to curves substantially orthogonal to the scan lines by arithmetic between reception signals for the sampling point at different time points. Each curve of the curves substantially orthogonal to the scan lines is constituted by a sequence of points for which a total of times taken for ultrasonic pulses to reach from two points fixed to the ultrasonic probe is substantially the same.

11 Claims, 13 Drawing Sheets

(56) References Cited

OTHER PUBLICATIONS

Trahey, G. E. et al., "Angle Independent Ultrasonic Detection of Blood Flow", IEEE Transactions on Biomedical Engineering, vol. 34, No. 12, pp. 965-967, (Dec. 1987).

Liebgott, H. et al., "Beamforming Scheme for 2D Displacement Estimation in Ultrasound Imaging", EURASIP Journal on Applied Signal Processing, pp. 1212-1220, (Aug. 2005).

Internatioanl Search Report Issued Dec. 28, 2009 in PCT/JP09/068995 filed Nov. 6, 2009.

* cited by examiner

FIG.2
(a)
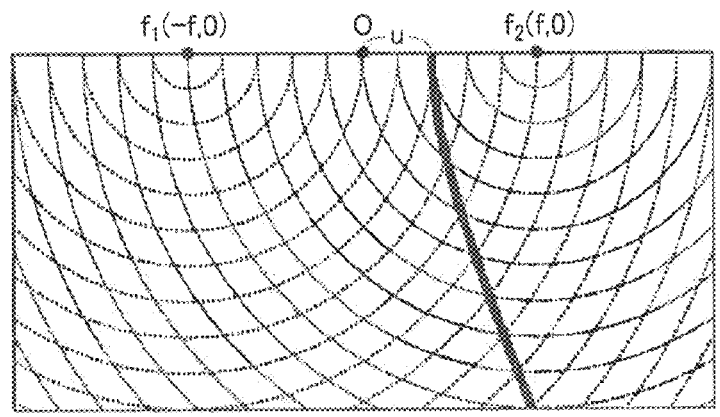
(b)
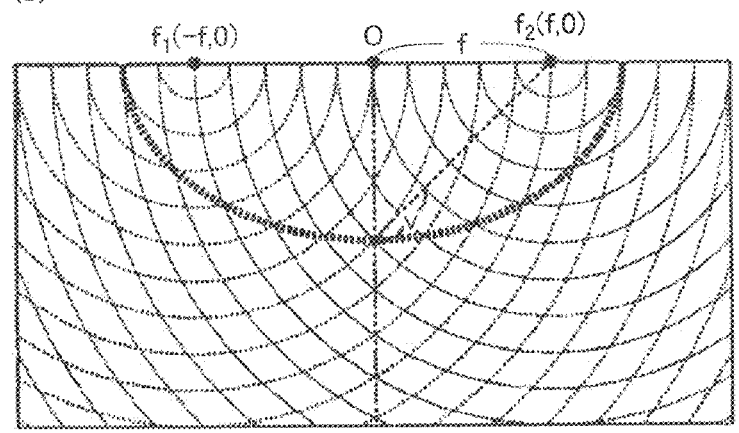
(c)
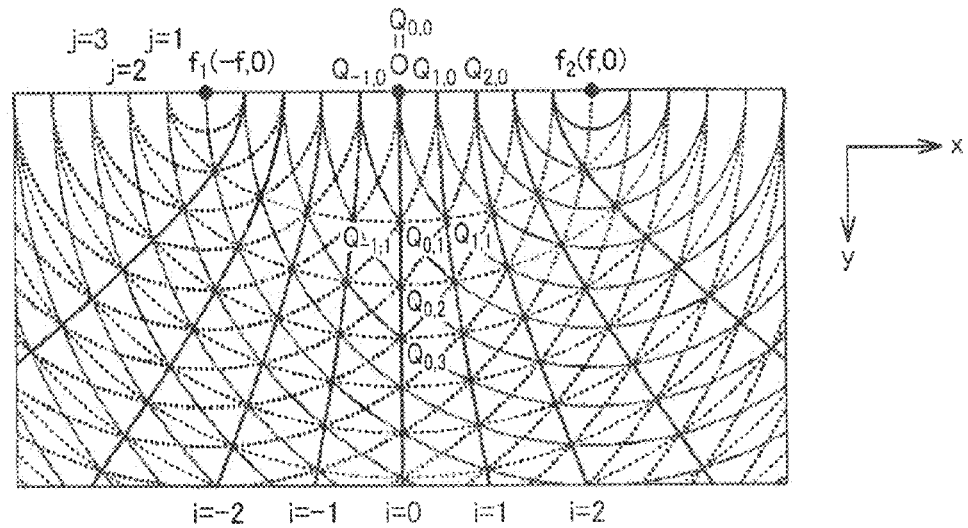

FIG.7
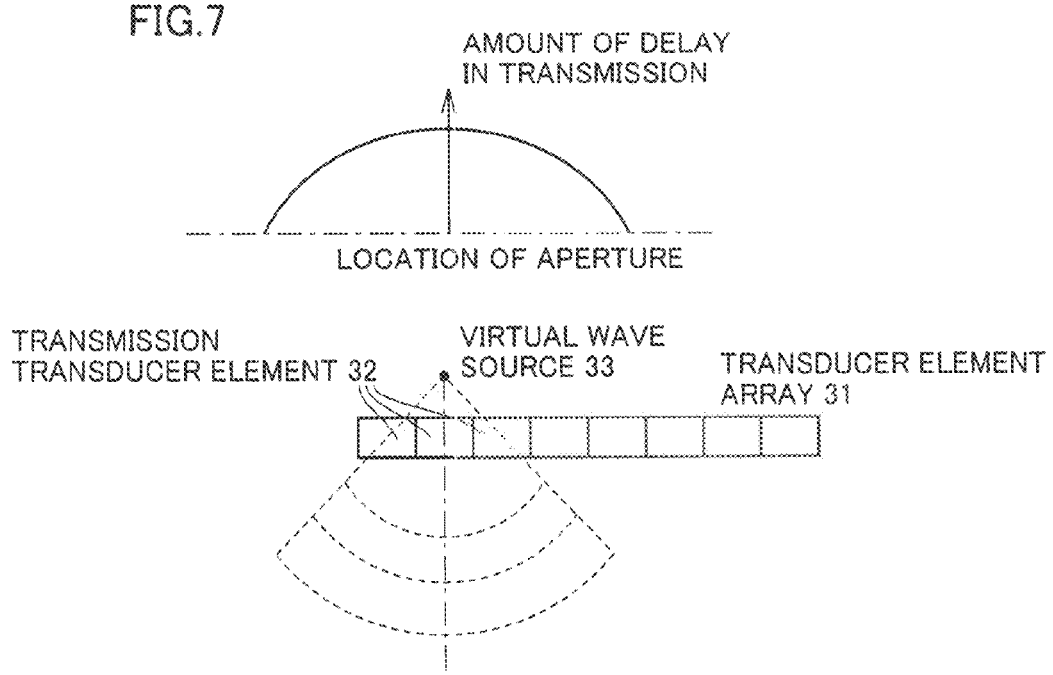
FIG.8
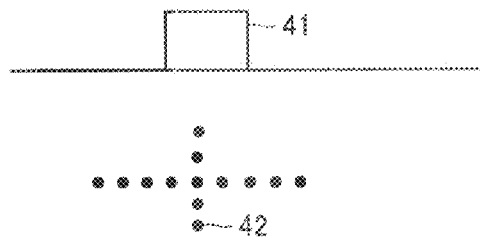
FIG.9
(a) MODULATION PATTERN
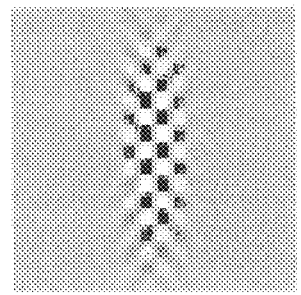
(b) MODULATION PATTERN
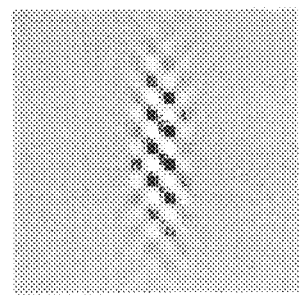

(a) PHASE DIFFERENCE IN RADIAL DIRECTION (b) PHASE DIFFERENCE IN CIRCUMFERENTIAL DIRECTION (c) PHASE DIFFERENCE IN RADIAL DIRECTION (d) PHASE DIFFERENCE IN CIRCUMFERENTIAL DIRECTION

LOCATION OF APERTURE OF TRANSMISSION
TRANSDUCER ELEMENT ARRAY

LOCATION OF APERTURE OF RECEPTION
TRANSDUCER ELEMENT ARRAY

LOCATION OF APERTURE OF RECEPTION
TRANSDUCER ELEMENT ARRAY

FIG.20
(a) 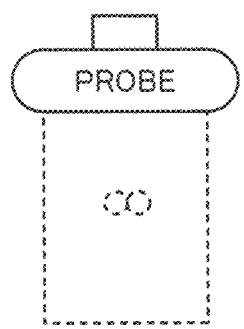
(b) 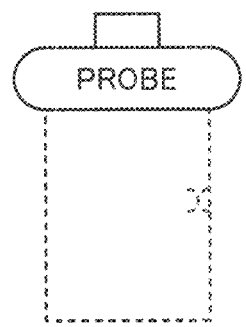
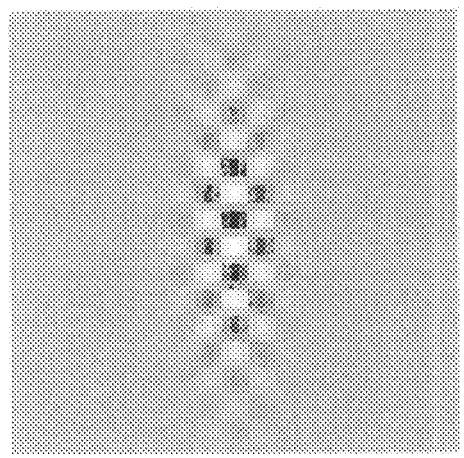
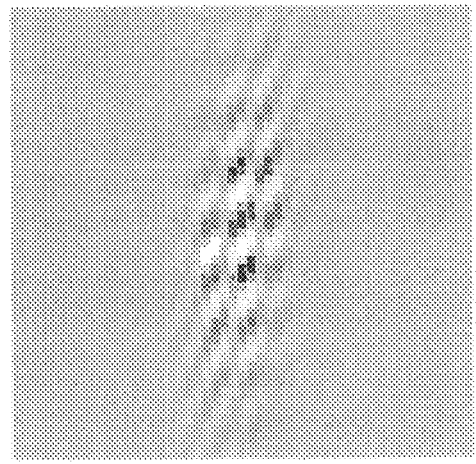

ULTRASONOGRAPHIC DIAGNOSTIC SYSTEM AND ULTRASONIC DIAGNOSTIC DEVICE

TECHNICAL FIELD

The present invention relates to an ultrasonic diagnostic system and an ultrasonic diagnostic device.

BACKGROUND ART

Recent ultrasonic diagnostic devices have a function of displaying an ultrasonic tomographic image (B mode image) obtained from a reflected echo resulting from a difference in reflectivity between tissues to indicate a tissue structure in a living body, as well as a function of measuring a blood flow velocity and a blood flow rate in a blood vessel and a heart using ultrasonic Doppler blood flowmetry or measuring a velocity or amount of motion of tissue portions such as motion of a cardiac wall and displaying information about them.

Further, recently, ultrasonic waves have begun to be used to measure hardness of tissue portions for tissue diagnosis. This is because hardness, i.e., an elastic property in a rough area is deeply associated with its pathological state. For example, it is known that a disease area is harder than a normal tissue in the case of sclerosing cancer such as breast cancer or thyroid cancer, liver cirrhosis, arteriosclerosis, and the like. Conventionally, information regarding such hardness is obtained from palpation. However, it is difficult to express objective information using palpation and palpation requires experienced doctors. To address this, in recent years, the following method has been utilized to determine hardness of a tissue. That is, the hardness of a tissue is determined from the magnitude of a strain caused in the tissue and measured using ultrasonic wave. The strain is caused therein by applying, from a body surface, static pressure or vibration with ultrasonic wave having a relatively low frequency. In particular, by incorporating the strain measurement function into an ultrasonic diagnostic device and simultaneously visualizing a tissue structure obtained by a conventional B mode image and a strain distribution, the disadvantage of palpation can be overcome and the tissue structure and the distribution of hardness can be compared and contrasted. Accordingly, a larger amount of information for diagnosis can be provided. Ultrasonic diagnostic devices having such a function have begun to be used mainly for diagnosis for mammary gland area.

The above-described velocity measurement for blood flow or the like and strain measurement with the use of ultrasonic wave are both performed based on a function of measuring a displacement using ultrasonic wave. For example, in measuring a distribution in blood flow velocity, a distribution of displacements of a tissue portion at different time points is calculated from ultrasonic echo signals obtained at the time points. Then, a value of a displacement at each point in the distribution of displacements is divided by a time interval between the time points of the measurement. In this way, a velocity distribution is found. Similarly, a strain distribution is found as follows. That is, the value of the displacement at each point in the displacement distribution found using ultrasonic wave is differentiated with respect to a distance between the points.

As such, the above-described measurement for velocity in blood flow and various functions of tissue motion, as well as the strain measurement for inspecting the hardness of a tissue are based on the function of measuring a displacement using ultrasonic wave. Hence, in recent ultrasonic diagnostic devices, such displacement measurement using ultrasonic wave has become an important technical issue.

A conventional ultrasonic diagnostic device transmits an ultrasonic wave to a body tissue, and finds a displacement from an echo signal reflected by the tissue. For example, in a pulse Doppler method, a color flow method, and the like, a pulse train of an ultrasonic wave is transmitted and reflected echo signals corresponding to different transmission pulse ultrasonic waves of the pulse train are compared to detect a time deviation (phase difference) between the reflected echo signals at each portion. This time deviation is caused due to a difference between times taken for the reflected ultrasonic waves to reach an ultrasonic reception location. The difference between the times is caused depending on a difference between the locations of a tissue in the ultrasonic propagating direction. The tissue has generated reflection echoes for portions thereof on the received echo signals corresponding to the different transmitted pulses. Hence, by multiplying this phase difference (=time difference) by acoustic velocity in the tissue, a difference between the locations of a corresponding portion, i.e., displacement, in the ultrasonic propagating direction is detected for the received echo signals of the different transmitted pulses. In actual detection of such a phase difference, a process of calculating is likely to be performed to detect the phase difference using frequency analysis between the reflected echo signals corresponding to the different transmitted pulses, such as correlation arithmetic or FFT (Fast Fourier Transform).

Further, in a continuous-wave Doppler method, a velocity component in the ultrasonic propagating direction is directly calculated using frequency analysis or the like, based on such a fact that a continuous ultrasonic wave is transmitted and reflected echo signals received are changed in wavelength by the velocity component in the ultrasonic propagating direction of the reflecting tissue due to an ultrasonic Doppler effect. In this case, the velocity component can be thus measured directly. In order to find a displacement, the velocity component may be integrated by a corresponding time interval.

These methods find a displacement or a velocity in the ultrasonic propagating direction. However, an actual tissue displacement does not necessarily take place only in the ultrasonic propagating direction. Hence, generally, during diagnosis, based on a B mode image visualized simultaneously, the ultrasonic propagating direction is matched to a direction of displacement estimated from a tissue structure, or the estimated direction of displacement is corrected with respect to the measured displacement or velocity. However, generally, it is difficult to estimate the direction of displacement at each portion in advance, which results in an error caused by the estimated direction.

Proposed to overcome such a disadvantage is a method of measuring two-dimensional or three-dimensional displacement and velocity using ultrasonic wave.

For example, Fox has proposed a method of providing two velocity components by means of compound scanning performed from two different locations in "Multiple crossed-beam ultrasound Doppler velocimetry", IEEE Trans. Sonics Ultrason., Vol. 25 pp. 281-286, 1978, (Non-Patent Document 1). However, this method suffers from a practical problem because it requires a transducer element array with a large aperture. An aperture of a transducer element array actually usable therefor has disadvantages such as limited visual field and insufficient precision provided by velocity composition.

Further, Trahey et al., has proposed a two-dimensional speckle tracking method based on a frame-to-frame correlation analysis, in "Angle independent ultrasonic detection of blood flow", IEEE Trans. Biomed. Eng., Vol. 34, pp. 965-967, December, 1987, (Non-Patent Document 2). This method is to perform two-dimensional correlation arithmetic between frames of B mode images captured at different time points, or two-dimensional correlation arithmetic of obtained sequences of reflected echo signals. In many ultrasonic diagnostic devices currently available, most part of a process for obtained signals, in particular, beam forming, detection, and the like are performed by means of digital processing. Hence, in the case of performing such two-dimensional correlation arithmetic, it is preferable to perform digital two-dimensional correlation arithmetic in view of precision and reliability of the process, compatibility to existing systems, and the like. Generally, in the digital two-dimensional correlation arithmetic, processing speed thereof, circuit scale for the process, and the like are greatly dependent on the number of data sampling. Hence, a smaller number of data sampling is preferable. Conversely, in the case of using the two-dimensional speckle tracking method, the number of data sampling is determined by its displacement detection precision and a measurement area. Hence, in order to increase the precision in displacement detection in a specific measurement area, the number of data sampling should be increased. Normally, when precision in displacement detection in each of two-dimensional directions is multiplied by N, the number of data sampling is increased by $N^2$. For example, in a normal ultrasonic diagnostic device, signals with ultrasonic reflection echoes are received at a relatively high sampling rate when creating B mode images. Hence, for the imaging thereof, the number of sampling (detection) is reduced. Further, an interval between scan lines of ultrasonic beams is relatively large. Hence, for the imaging, the number of scan lines for displaying is increased in the ultrasonic scan line direction by interpolation or the like. When obtaining two-dimensional correlation between frames of B mode images displayed in accordance with the two-dimensional speckle tracking method, precision for displacement is the same in degree as that for the image on pixels. In this case, the precision for displacement is reduced because the number of sampling is reduced in the direction of reflected ultrasonic echo reception signals measurable using a normal Doppler method or the like. Hence, with this method, a displacement component in a direction different from that in the conventional art can be detected, but the precision of detecting a displacement component in the direction in which it can be attained in the conventional art is decreased greatly. Further, the two-dimensional speckle tracking method may be performed using reflected ultrasonic echo signals prior to detection. In this case, the precision of detecting the displacement component can be secured in the direction in which it can be attained in the conventional art. However, the number of data sampling becomes enormous, with the result that the two-dimensional speckle tracking method cannot be implemented in the scale of the conventional ultrasonic diagnostic devices. Thus, the two-dimensional speckle tracking method is only applicable to detection of motion of a tissue portion displaced relatively greatly, disadvantageously.

As a relatively new method for two-dimensional displacement measurement, Japanese National Patent Publication No. 2001-503853 (Patent Document 1) discloses a method for providing lateral modulation in a received beam pattern by means of a coherent process using two sub-apertures provided in a transducer element array. In this method, spatial modulation is provided to reception sensitivity in two directions by means of interference of the two reception sub-apertures, thereby allowing for detection of displacement components in the two modulation directions. This method can provide an ultrasonic wave with a wavelength spatially modulated in its propagating direction substantially as much as in the direction of a reflected ultrasonic echo in which the detection of displacement can be attained in the conventional art. Hence, a displacement component can be measured in a direction orthogonal to the ultrasonic propagation without greatly decreasing the precision for displacement in the ultrasonic propagating direction as compared with the precision for displacement in the conventional art. However, in this method, spatial resolution is decreased, disadvantageously.

U.S. Pat. No. 6,859,076 (Patent Document 2) discloses a method for improving measurement precision in the method described in Japanese National Patent Publication No. 2001-503853 (Patent Document 1). However, in the method disclosed therein, a process including calculation of 4th order moment for reflected ultrasonic echo reception signals is substantially performed. Accordingly, an amount to be processed is increased. This makes it difficult to implement the method in a conventional ultrasonic diagnostic device, disadvantageously.

Further, a method different from that of U.S. Pat. No. 6,859,076 (Patent Document 2) in transmission/reception beam formation is described in Liebgott, et al., "Beamforming Scheme for 2D Displacement Estimation in Ultrasound Imaging" EURASIP Journal on Applied Signal Processing 2005: 8, pp 1212-1220, August, 2005 (Non-Patent Document 3).

PRIOR ART DOCUMENTS

Patent Documents

Patent Document 1: Japanese National Patent Publication No. 2001-503853
Patent Document 2: U.S. Pat. No. 6,859,076

Non-Patent Documents

Non-Patent Document 1: Fox "Multiple crossed-beam ultrasound Doppler velocimetry", IEEE Trans. Sonics Ultrason., Vol. 25, pp. 281-286, 1978
Non-Patent Document 2: Trahey, et al., "Angle independent ultrasonic detection of blood flow", IEEE Trans. Biomed. Eng., Vol. 34, pp. 965-967, December, 1987
Non-Patent Document 3: Liebgott, et al., "Beamforming Scheme for 2D Displacement Estimation in Ultrasound Imaging" EURASIP Journal on Applied Signal Processing 2005: 8, pp. 1212-1220, August, 2005

SUMMARY OF THE INVENTION

Problems to be Solved by the Invention

The present invention is made to overcome the disadvantages of the two-dimensional displacement measurement methods employing ultrasonic wave as disclosed in Patent Document 1, Patent Document 2, and Non-Patent Document 3, and provide a two-dimensional displacement measurement method suitable for implementation in a conventional ultrasonic diagnostic device.

Referring to FIG. 13, the following describes a principle of each of the conventional two-dimensional displacement measurement methods concerned with Patent Document 1, Patent Document 2, and Non-Patent Document 3.

A pulse generator 1201 generates a transmission pulse train.

Based on the transmission pulses generated by pulse generator 1201, transmission beam former 1202 generates a pulse driving voltage for each transducer element in a transmission transducer element array 1203 in order to transmit an ultrasonic beam to measurement target 1204. On this occasion, as normally done in ultrasonic diagnostic devices, transmission beam former 1202 can focus to converge the ultrasonic beam to be transmitted from an aperture of transmission transducer element array 1203. The focusing is performed by delaying a driving pulse voltage to be supplied to a corresponding transducer element of transmission transducer element array 1203 as shown in FIG. 14, for example. FIG. 14 shows exemplary delay for minimizing the width of the transmission ultrasonic beam at a point designated on the central axis of the aperture of transmission transducer element array 1203. Further, transmission beam former 1202 also can adjust the amplitudes of the pulse driving voltages for the transducer elements to achieve curved amplitude distribution of the transmission signals with the peak thereof at the center of the aperture as shown in, for example, FIG. 15 in order to prevent occurrence of side lobe of the ultrasonic beam to be transmitted (this is referred to as "transmit apodization" as well known in the present technical field). Further, the transmission ultrasonic beam can be oriented toward a desired direction depending on an amount of delay provided by transmission beam former 1202 (this is referred to as "beam steering" as well known in the present technical field).

Each transducer element of transmission transducer element array 1203 is driven by the received driving pulse voltage to transmit an ultrasonic pulse to measurement target 1204. When the delay is provided by transmission beam former 1202 as shown in FIG. 14, the transmission ultrasonic pulses to be transmitted are spatially converged into an ultrasonic beam, which is then propagated in a measurement target 1204.

The ultrasonic pulses thus transmitted to measurement target 1204 are reflected by tissues in measurement target 1204. The reflected echo ultrasonic waves are received by each reception transducer element of a reception transducer element array 1205. Each reception transducer element generates a reception echo signal. The reception echo signals from reception transducer elements of reception transducer element array 1205 are input to a reception beam former 1206 and are amplified at signal amplitude amplification factors different for the respective reception transducer elements so as to obtain reception sensitivities dependent on a location of the aperture of reception transducer element array 1205 (this is referred to as "receive apodization" as well known in the present technical field). Thereafter, they are added to obtain an added signal, which is then sent to a displacement detecting processor 1207.

In the methods described in Patent Document 1 and Patent Document 2, characteristic apodization with two peaks is provided to the aperture shown in FIG. 16. Further, Patent Document 1 discloses an example in which the reception echo signals from reception transducer element array 1205 are delayed in reception time by reception beam former 1206 as shown in FIG. 17. The reception echo signals having been through the apodization and the application of time delay are added and input to displacement detecting processor 1207. Displacement detecting processor 1207 calculates a two-dimensional displacement and the result of calculation is displayed on a display 1208.

A feature of such two-dimensional displacement measurement lies in that two sub-apertures are substantially formed on the reception aperture for the echo ultrasonic waves, by means of the apodization for the reception echo signals from the transducer elements of reception transducer 1205 in reception beam former 1206 as shown in FIG. 16. When the reception signals from such two sub-apertures are added and used, reception sensitivity distribution is spatially modulated due to an interference effect of the two apertures. This will be described with reference to FIG. 18 and FIG. 19. FIG. 18 shows sub-apertures 1701, 1702, which are substantially generated due to the receive apodization. With the apodization shown in FIG. 16 and the delay shown in FIG. 17 in reception beam former 1206, ultrasonic waves received by reception sub-apertures 1701, 1702 have maximum sensitivities for plane waves having directivity for a direction 1703 and a direction 1704, respectively. Wavefronts 1705, 1706 of these plane waves are shown schematically. By the interference between plane waves 1705, 1706 received by reception sub-apertures 1701, 1702, the added reception echo signal is provided with a sensitivity distribution two-dimensionally spatially modulated. FIG. 19 shows this state. FIG. 19 shows wavefronts 1705, 1706 of the plane waves mainly received by reception sub-apertures 1701, 1702. The interference of the two plane waves causes an interference pattern illustrated in hatch in FIG. 19. A manner of modulation on a constant line in the x direction is indicated by 1802. A manner of modulation on a constant line in the z direction is indicated by 1803. Thus, spatial waves are generated in the x direction and the z direction orthogonal to each other as shown in FIG. 19, by the interference between the plane waves having the two directions and high reception sensitivity for reception sub-apertures 1701, 1702. This is reflected in the added reception echo signal sent from reception beam former 1206, specifically, the added reception echo signal has a sensitivity distribution in the two directions spatially orthogonal to each other.

When a reflector (tissue) of measurement target 1204 is moved while the reception sensitivity distribution is thus two-dimensionally spatially modulated, the added reception echo signal of the ultrasonic echoes from the moving reflector having reflected the transmitted ultrasonic beam is changed depending on the modulation of the spatial distribution of the reception sensitivity and the moving velocity of the reflector. Hence, the added reception echo signal, output from reception beam former 1206, is acquired for each of the transmission pulses generated by transmission pulse train 1201. From the change thereof, displacements and velocity components can be detected in the two modulation directions of the reception sensitivity spatial distribution.

According to Patent Document 2, an added reception signal R(n) for the n-th pulse of a transmission pulse train with a pulse interval $T_p$ is changed in proportion to:

[Formula 1]

$$R(n) \sim \cos\left(2\pi \frac{2v_z}{\lambda} T_p n\right) \cos\left(2\pi \frac{v_x}{X_p} T_p n\right) \quad (1)$$

Here, $\lambda$ represents the wavelength of the ultrasonic wave used. $X_p$ represents a cycle of spatial modulation orthogonal to the ultrasonic propagation and caused by the interference between the two reception sub-apertures 1701, 1702. Further, $v_x$ represents a velocity in the aperture plane direction, and $v_z$ represents a velocity in the ultrasonic propagating direction. Furthermore, a displacement $\Delta x$ in the aperture plane direction and a displacement $\Delta z$ in the ultrasonic propagating direction, both of which are caused during pulse interval $T_p$, have the following relations with the velocities in their corresponding directions:

[Formula 2]

$$v_x = \frac{\Delta x}{T_p} \quad (2\text{-}1)$$

$$v_z = \frac{\Delta z}{T_p} \quad (2\text{-}2)$$

Using these relations, displacement detecting processor 1207 finds the velocity or displacement in the aperture plane direction, and the velocity or displacement in the ultrasonic propagating direction. Generally, a larger number n of pulses is required to find each of the different cycles precisely from the composite signal with the double cycles as indicated in Formula (1). This is not preferable because increase in the number of transmission pulses required for the measurement will result in slow response in real time operation such as decreased frame rate when applied to an ultrasonic diagnostic device. Patent Document 2 discloses a method for separating and finding velocity or displacement in the aperture plane direction and velocity or displacement in the ultrasonic propagating direction, using a 4th-order moment for an added signal sequence R(n). Further, Patent Document 1 discloses that: the velocity or displacement in the aperture plane direction perpendicular to the ultrasonic propagation is found by performing cross-correlation arithmetic of added signal sequence R(n) obtained when changing directions 1703, 1704 of plane waves for which reception sub-apertures 1701, 1702 mainly have sensitivity and performing normal reception beam forming in reception beam former 1206, whereas the velocity or displacement in the ultrasonic propagating direction is found using the conventional Doppler method.

In this way, the velocities or displacements in the two directions can be estimated from the change in the added reception echo signals for the pulse trains from the pulse generator. In addition, velocity or displacement distributions of the tissue located in the direction of the transmission ultrasonic beam can be estimated in the two directions in a manner similar to the conventional color flow method. By transmission beam former 1202 steering the transmission ultrasonic beam, two-dimensional velocity or displacement distributions in the two directions are calculated and are displayed on display 1208.

In the description above, the transmission ultrasonic beam is converged by focusing but the reception ultrasonic beam is not focused. Hence, reception sensitivity is widely distributed in measurement target 1204 while being modulated.

In contrast, Non-Patent Document 2 describes a method of focusing during reception instead of focusing during transmission. However, in this case, in order to maintain a constant modulation interval in the direction perpendicular to the ultrasonic propagation, an interval between reception sub-apertures 1701, 1702 needs to be changed in accordance with a reception focusing location. As described in Non-Patent Document 2, spatial modulation cycle $X_p$ or spatial modulation frequency $f_x$ in the direction perpendicular to the ultrasonic propagation is approximately determined as follows using an ultrasonic propagating direction focus depth z, an ultrasonic wavelength $\lambda$, and a distance $d_x$ between reception sub-apertures 1701, 1702:

[Formula 3]

$$X_p = \frac{1}{f_x} = \frac{2\lambda z}{d_x} \quad (3)$$

As understood from Formulae (1) and (3), it is preferable that spatial modulation cycle $X_p$ is defined to be small and spatial frequency $f_x$ is defined to be large in order to increase the precision for the displacement and velocity in the direction perpendicular to the ultrasonic propagation. For this, distance $d_x$ between the reception sub-apertures is preferably defined to be large. To attain this, the reception aperture needs to have a size to secure distance $d_x$ required between the reception sub-apertures to increase the precision for the displacement in the direction perpendicular to the ultrasonic propagation. Accordingly, a large ultrasonic reception aperture needs to be defined in order to increase the precision for the velocity and displacement measurement in the direction perpendicular to the ultrasonic propagation. In doing so, it is preferable to perform the above-described steering operation in the ultrasonic beam forming because there is a production restriction as to the number of transducer elements on the reception transducer element array, which results in insufficient distance secured between the reception sub-apertures in a method of forming a reception aperture using a part of the reception transducer element array, such as linear scanning in the conventional art.

Further, in order to use the above-described displacement measurement method for calculation of the velocity and displacement distributions, it is preferable that precision for the velocity and displacement measurement and the spatial resolution for the measured area are high. This spatial resolution depends on the width of the ultrasonic beam focused. Hence, when velocity distribution and displacement distribution are measured with the focusing being performed for only one of the transmission and the reception, spatial resolution for the distribution is deteriorated in the lateral direction as compared with the conventional color flow method in which a formed beam is focused upon both the transmission and reception. To avoid this, ultrasonic wave focusing needs to be performed to obtain beams having sufficiently thin widths for the transmission and reception.

However, the inventor has studied and found that when steering the ultrasonic wave to scan for angles with the ultrasonic beam with focusing being provided upon the transmission and reception, the sensitivity distribution pattern caused by the interference between the sub-apertures is changed depending on a steering direction.

FIG. 20 shows, in a hatch pattern, a reception sensitivity distribution obtained as a result of simulation performed using a method similar to that of Non-Patent Document 3 with steering and focusing being performed upon the transmission and reception.

FIG. 20(*a*) shows a reception sensitivity obtained when the transmission/reception beam is set just below the center of the aperture by steering. Referring to the central part of the screen, it is appreciated that modulation is applied in the vertical and horizontal directions in an orderly manner.

Meanwhile, FIG. 20(*b*) shows a case where a transmission/reception beam is generated with steering at a lower left portion relative to the aperture center in the screen. Although the modulation is applied in two directions, they are inclined unlike the directions at the center.

As such, when steering an ultrasonic beam focused to detect velocity and displacement distributions with high precision, a direction of spatial modulation is changed depending on the steering direction. Accordingly, errors occur in detecting velocities and displacements at an end portion of the screen using such a conventional method of measuring the velocities and displacements in the two-dimensional directions orthogonal to each other. As a result, the velocity and displacement distributions cannot be obtained satisfactorily, disadvantageously.

Further, measurement involving a complex process such as the one in Patent Document 2 is not suitable for implementation on an ultrasonic device due to the complexity of the process.

The present invention is to provide a two-dimensional displacement measurement method overcoming the disadvantages of the conventional art and suitable for implementation on a conventional ultrasonic diagnostic device. Examples of the disadvantages include: low spatial resolution in the lateral direction during measurement of velocity and displacement distributions; decreased precision in detecting the velocities and displacements at an end portion; and a complex process.

In addition, referring to the publications of the conventional art, the description above has illustrated the case where the receive apodization is provided to set the two reception sub-apertures 1701, 1702, thereby applying modulation to the spatial distribution of the reception sensitivity in the directions orthogonal to each other. However, the velocities or displacements can be measured in the two directions similarly as follows. That is, apodization to the transmission aperture is provided to set two transmission sub-apertures. In this way, in addition to a change as the intrinsic ultrasonic wave propagation, the transmission ultrasonic beam is modulated in the direction perpendicular to the ultrasonic propagation, i.e., the width direction of the ultrasonic beam by interference of the two transmission sub-apertures. Namely, the present invention also provides a method suitable for a configuration for laterally modulating the transmission beam in this way. In particular, when combining transmit apodization and receive apodization to enhance an effect of the lateral modulation, the present invention can employ a configuration suitable for simultaneously combining each apodization and each focusing of reception and transmission beam. Accordingly, spatial resolution and sensitivity can be improved at the same time when measuring the velocities and displacements.

Means for Solving the Problems

An ultrasonic diagnostic system in an aspect of the present invention includes an ultrasonic probe constituted by a group of ultrasonic transducer elements arranged in at least one direction; a beam forming unit for forming acoustic field sensitivity modulated in a direction substantially orthogonal to a group of scan lines in a subject by focusing an ultrasonic wave on a sequence of sampling points existing along the group of scan lines, and applying delay and apodization on a transmission/reception signal of each of the ultrasonic transducer elements; and a detecting unit for detecting displacements in at least two directions at each of the sampling points by arithmetic between reception signals for the sampling point at different time points, the detecting unit detecting displacements at the sampling point in a direction tangential to the group of scan lines and in a direction tangential to a group of curves substantially orthogonal to the scan lines, the group of curves substantially orthogonal to the group of scan lines being a group of curves in the subject, each of the curves being constituted by a sequence of points for which a total of times taken for ultrasonic pulses to reach from two points fixed to the ultrasonic probe is substantially the same.

Preferably, the group of scan lines is a set of curves or straight lines selected so that a difference between the times taken for the ultrasonic pulses to reach from the two points fixed is substantially the same, and the difference between the times taken for the ultrasonic pulses to reach from the two points fixed has a constant difference between adjacent curves or adjacent straight lines.

Preferably, the sampling points for finding the displacements are arranged on intersections of the group of scan lines and the group of curves substantially orthogonal to the group of scan lines, the group of curves substantially orthogonal to the group of scan lines is a set of curves selected so that a total of the times taken for the ultrasonic pulses to reach from the two points fixed is substantially the same, and the total of the times taken for the ultrasonic pulses to reach the curves from the two points fixed has a constant difference between adjacent curves.

Preferably, the group of scan lines is a group of hyperbolas assuming, as common focal points, the two points fixed to the ultrasonic probe, and the group of curves substantially orthogonal thereto is a group of ellipses assuming the two points as common focal points.

Preferably, the group of scan lines is a group of asymptotes of hyperbolas assuming, as common focal points, the two points fixed to the ultrasonic probe, and the group of curves substantially orthogonal thereto is a group of ellipses assuming the two points as common focal points.

Preferably, the group of scan lines is a group of straight lines each radially extending through one point fixed to the ultrasonic probe, and the group of curves substantially orthogonal thereto is a group of concentric circles each assuming the one point as a common middle point.

Preferably, the ultrasonic probe constituted by the group of ultrasonic transducer elements focuses an ultrasonic wave by means of aperture synthesis achieved by transmission of an ultrasonic wave by at least one or more ultrasonic transducer elements of the group of ultrasonic transducer elements, and reception by ultrasonic transducer elements larger in number than the ultrasonic transducer elements that transmit.

Preferably, the ultrasonic transducer elements transmitting an ultrasonic wave are two or more ultrasonic transducer elements, and the two or more ultrasonic transducer elements transmit ultrasonic waves such that a sonic wave obtained by combining the ultrasonic waves transmitted from the two or more ultrasonic transducer elements becomes a spherical wave or an effectively cylindrical wave coming from a wave transmission surface of the group of ultrasonic transducer elements and centered at a virtual sound source defined opposite to the wave transmission side.

Preferably, the detecting unit has a correlation calculating unit for finding a displacement in a direction along the group of scan lines by performing cross-correlation arithmetic between echo signal sequences constituted by echo signal values at a plurality of sampling points along the scan lines at the different time points, and finding a displacement in a direction along the group of curves substantially orthogonal to the scan lines by performing cross-correlation arithmetic between echo signal sequences constituted by echo signal values at sampling points along the curves substantially orthogonal to the scan lines at the different time points.

Preferably, the detecting unit has a correlation calculating unit for finding a displacement in a direction along the group of scan lines by performing cross-correlation arithmetic between echo signal sequences constituted by echo signal values at different sampling points in the direction along the scan lines at the different time points, and finding a displacement in a direction along the group of curves substantially orthogonal to the scan lines by performing cross-correlation arithmetic between echo signal sequences constituted by echo signal values at different sampling points along the curves substantially orthogonal to the scan lines at the different time points.

An ultrasonic diagnostic device in an aspect of the present invention includes: an ultrasonic probe constituted by a group of ultrasonic transducer elements arranged in at least one direction; a beam forming unit for forming acoustic field sensitivity modulated in a direction substantially orthogonal to a group of scan lines in a subject by focusing an ultrasonic wave on a sequence of sampling points existing along the group of scan lines, and applying delay and apodization on a transmission/reception signal of each of the ultrasonic transducer elements; and a detecting unit for detecting displacements in at least two directions at each of the sampling points by performing arithmetic between reception signals for the sampling point at different time points, the detecting unit detecting displacements at the sampling point in a direction tangential to the group of scan lines and in a direction tangential to a group of curves substantially orthogonal to the scan lines, the group of curves substantially orthogonal to the group of scan lines being a group of curves in the subject, each of the curves being constituted by a sequence of points for which a total of times taken for ultrasonic pulses to reach from two points fixed to the ultrasonic probe is substantially the same.

Effects of the Invention

As described above, the present invention achieves two-dimensional displacement distribution measurement and two-dimensional velocity distribution measurement with high spatial resolution and high precision.

BRIEF DESCRIPTION OF THE DRAWINGS

FIG. 2 shows a relation of sampling points in the embodiment of the present invention.

FIG. 7 illustrates another transmission method in the another preferable embodiment of the present invention.

FIG. 8 shows a model of simulation to illustrate an effect of the embodiment of the present invention.

FIG. 9 shows a simulation result of a reception signal pattern in the embodiment of the present invention.

FIG. 20 shows disadvantages of the conventional art.

MODES FOR CARRYING OUT THE INVENTION

The present invention is to correct a change, caused depending on a steering direction, in a direction in which spatial modulation is applied, when steering an ultrasonic beam focused for detection of velocity and displacement distributions with high precision.

Figure 1:
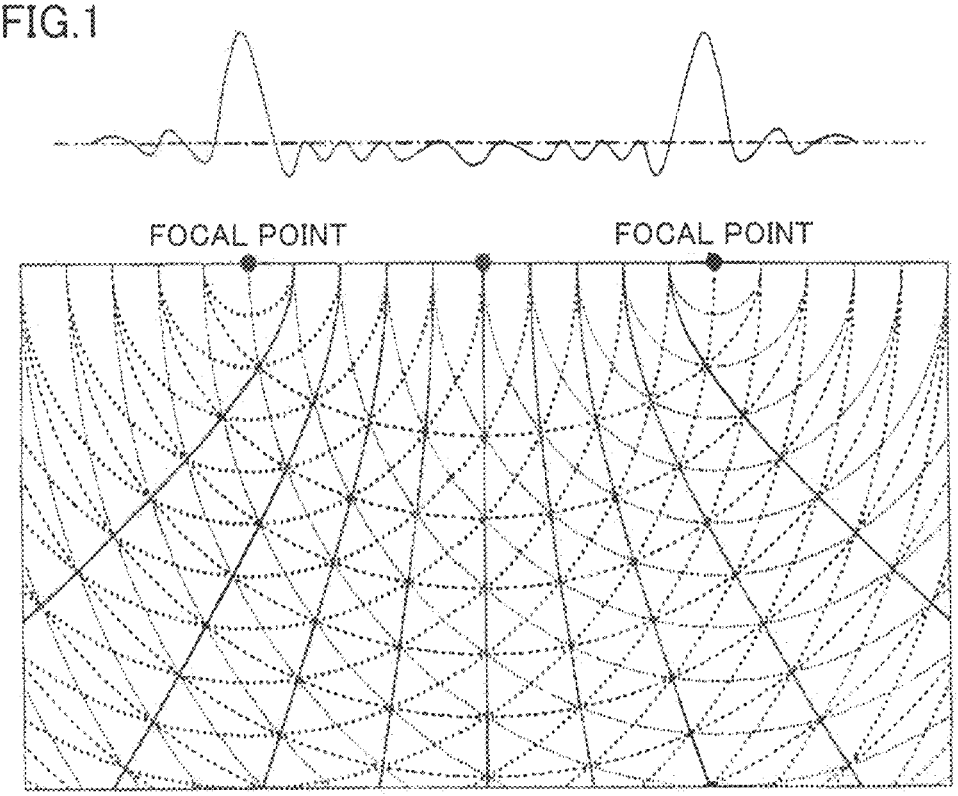
FIG. 1 shows a principle of an embodiment of the present invention.

FIG. 1 schematically shows transmission or reception ultrasonic waves with apodization with two peaks being applied to a transmitting or reception aperture for the ultrasonic waves. The transmission/reception ultrasonic waves are approximately two spherical waves (two-dimensionally, concentric circular waves) generated or converged from the two apexes or centroids when the widths of rises substantially constituting the two peaks in the apodization are small. As well known, an interference pattern generated by interference of these two waves is constituted by groups of curves, i.e., hyperbolas and ellipses. Each of the groups assumes the apexes or the centroids as common two focal points (confocals). Namely, to such transmission/reception ultrasonic waves with the apodization, (two types of) spatial modulations are applied in two directions substantially orthogonal to each other, in the vicinity of each of spatial points. The two modulation directions are tangential directions of a hyperbola and an ellipse extending through each point. For each point located on and along a certain hyperbola or ellipse, only one of the above-described two types of spatial modulations is applied.

For example, assuming waves generated from the two confocals and having the same wavelength $\lambda$, the modulation is approximately as follows at points distant away by r1, r2 from the two confocals, with a portion concerned with common time fluctuation being excluded:

[Formula 4]

$$\cos\frac{2\pi r_1}{\lambda} + \cos\frac{2\pi r_2}{\lambda} \quad (4)$$

Using a half S of the total of the distances from the two focal points and a half $\rho$ of a difference between the distances from the two focal points, the following formula is obtained with regard to the location. It should be noted that each of $\delta_1$ and $\delta_2$ represents an appropriate phase difference, and $C_0$ represents a constant not depending on the location of each point.

[Formula 5]

$$\sim C_0 \cos\left(\frac{2\pi S}{\lambda} + \delta 1\right)\cos\left(\frac{2\pi \rho}{\lambda} + \delta 2\right) \quad (5-1)$$

$$S = \frac{r_1 + r_2}{2} \quad (5-2)$$

$$\rho = \frac{r_1 - r_2}{2} \quad (5-3)$$

As well known, a hyperbola is a curve with a constant difference between distances from two focal points. At points on the same hyperbola, modulation is applied depending on a change of S with $\rho$ being constant. Further, an ellipse is a curve with the total of its distances from two focal points being constant. At points on the same ellipse, modulation is applied depending on a change of ρ with S being constant.

As such, when the transmission/reception aperture is provided with the apodization with two peaks, the two types of modulation patterns for the spatial distribution of reception sensitivity substantially conform to the group of hyperbolas and the group of ellipses. It is appreciated that as shown in FIG. 20, a direction in which a modulation is applied is changed depending on a location.

Thus, unlike in the conventional art, i.e., instead of finding displacements by dividing the two-dimensional displacement directions into two axes orthogonal to each other and spatially fixed or simply dividing them into an ultrasonic beam direction and a direction perpendicular to the beam, displacements can be found by dividing them into the direction of each hyperbola extending through a measurement point and the tangential direction of each ellipse extending though the measurement point with the two apexes or two centroids in the apodization with two peaks being assumed as confocals. In this way, a displacement can be measured substantially along the two-dimensional spatial modulation pattern. As a result, precision in the displacement measurement is not deteriorated.

As with Formula (1), the following formula expresses a change in an echo reception signal corresponding to an n-th transmission pulse and coming from a specific point P in a measurement target, with a pulse interval being considered as $T_p$:

[Formula 6]

$$R(n) \sim \cos\left(2\pi \frac{2v_h}{X_h} T_p n\right) \cos\left(2\pi \frac{2v_e}{X_e} T_p n\right) \quad (6)$$

Here, $v_h$ represents a velocity in the direction along the hyperbola, and $v_e$ represents a velocity in the direction along the ellipse. $X_h$ represents substantially the ultrasonic wavelength in a spatial modulation cycle in the direction along the hyperbola. $X_e$ may represent substantially the ultrasonic wavelength when the width of each peak in the apodization is small in a spatial modulation cycle in the direction along the ellipse, but may be one corrected depending on the width of the peak.

On this occasion, when an echo reception signal is received at substantially the same time from a point P' located on the same ellipse as that for the foregoing point, a change in the reception signal is expressed as follows because the spatial modulation in the hyperbola direction does not effectively affect on the same ellipse as described above:

[Formula 7]

$$R'(n) \sim \cos\left(2\pi \frac{2v_h}{X_h} T_p n\right) \cos\left(2\pi \frac{2v_e}{X_e} T_p n + \delta e\right) \quad (7)$$

Here, $\delta_e$ represents a phase difference caused due to a difference between the locations of the points on the ellipse.

In particular, with a point $P_e$ being taken on an ellipse in which $\delta_e$ is π/4, a corresponding signal $R^e(n)$ is expressed as follows:

[Formula 8]

$$R^e(n) \sim \cos\left(2\pi \frac{2v_h}{X_h} T_p n\right) \sin\left(2\pi \frac{2v_e}{X_e} T_p n\right) \quad (8)$$

Using reception signals R(n) and $R^e(n)$, a velocity in the tangential direction of the ellipse can be independently calculated. For example, normal Doppler phase detection may be performed using a signal obtained by dividing R(n) and $R^e(n)$. Further, by obtaining a cross-correlation between R(n) and $R^e(n)$, a velocity component can be detected. For improved detection precision, reception signals for a plurality of points adjacent to one another on the same ellipse may be compared to one another.

For example, the velocity in the ellipse direction can be found as follows by performing cross-correlation arithmetic of signal R(n) for point P and signal $R^e(n)$ for point $P_e$, point P and point $P_e$ being different by a phase of π/4 on the ellipse:

[Formula 9]

$$v_e = \frac{X_e}{4\pi T_p} \tan^{-1}\left[\frac{\sum_n (R(n)R^e(n+1) - R(n+1)R^e(n))}{\sum_n (R(n)R(n+1) + R^e(n+1)R^e(n))}\right] \quad (9)$$

Similarly, only the velocity in the tangential direction of the hyperbola can be found using echo reception signals obtained from a plurality of points located on the same hyperbola. In particular, the velocity in the hyperbola direction is determined as follows by performing cross-correlation arithmetic of signal R(n) for point P and signal $R^h(n)$ for a point $P_h$ located on the same hyperbola with a phase difference of π/4 in the following manner:

[Formula 10]

$$v_e = \frac{X_h}{4\pi T_p} \tan^{-1}\left[\frac{\sum_n (R(n)R^h(n+1) - R(n+1)R^h(n))}{\sum_n (R(n)R(n+1) + R^h(n+1)R^h(n))}\right] \quad (10)$$

In the description above, the detection of velocities has been explained, but apparently, a displacement taking place in a predetermined transmission pulse interval can be detected as well. Further, it is apparent from the description above that the two groups of curves described above are essentially constituted by: a group of curves in which a total of distances from the two apexes or centroids in the apodization with two peaks is substantially constant and a total of times taken for the ultrasonic pulses to reach points on the curves from the two apexes or centroids is substantially the same; and a group of curves in which a difference between distances from two apexes or centroids in the apodization with two peaks is substantially constant and a difference between times taken for the ultrasonic pulses to reach points on curves from the two apexes or centroids is substantially the same. Even if the groups are slightly deviated from the exact group of hyperbolas and group of ellipses, there is an effect. Particularly, an asymptote exists for a hyperbola. When being distant further away from its focal point, the hyperbola can be partially approximated by the asymptote. Hence, at such a distant location, the hyperbola can be partially replaced with the asymptote, effectively. Hereinafter, this asymptote having partially replaced the hyperbola will be referred to as "substantial hyperbola". Similarly, an ellipse distant away from the focal point can be partially replaced with a circle. Hence, generally, the term "ellipse" used herein is intended to indicate an ellipse including such a circle, or in some case, the ellipse including an approximated circle is referred to as "substantial ellipse".

Further, in a preferable embodiment of the present invention, spatial resolution for distribution measurement is improved by focusing on, as sampling points, the intersections of the group of hyperbolas and the group of ellipses both having the common two focal points, upon transmission and reception. Unlike the conventional art of focusing only upon reception or transmission, focusing is performed substantially simultaneously upon the reception and the transmission. Accordingly, velocity and phase are detected using echo signals from vicinities of the sampling points to improve spatial resolutions for velocity and phase distributions. Hence, a diagnosis image more precise than that provided by the conventional art can be provided. At the same time, two-dimensional velocity components or two-dimensional displacement components are measured with a simple process without decreasing precision in measurement, by independently calculating a velocity component or a displacement component along a hyperbola from a plurality of sampling points adjacent to each other on the same hyperbola and calculating a velocity component or a displacement component along an ellipse from a plurality of sampling points on the same ellipse.

By allocating the sampling points at the intersections of the group of substantial hyperbolas and the group of substantial ellipses, processes can be simply performed, between a plurality of sampling points along a substantial hyperbola and between a plurality of sampling points along a substantial ellipse, in the vicinity of targeted sampling points.

Particularly preferably, the two groups of curves thus determining the sampling points are determined such that: the group of hyperbolas is a set of curves or straight lines selected so that a difference between times taken for ultrasonic pulses to reach from the two apexes or centroids in the apodization with two peaks is substantially the same, the difference in value between the times taken for the ultrasonic pulses to reach from the two points is constant between adjacent curves or straight lines; the group of ellipses is a set of curves selected so that a total of the times taken for the ultrasonic pulses to reach from the two points is substantially same; and the total of the times taken for the ultrasonic pulses to reach from the two points is constant between adjacent curves.

As known from Formulae (5-1)-(5-3), the two-dimensional spatial modulation pattern caused by the apodization with two peaks can be described using the total of the distances from the two apexes or centroids, and the difference between the distances of the two apexes or centroids. Further, generally, a hyperbola and an ellipse can be distinguished from each other by the locations of the two focal points as well as the total of distances from the two focal points and the difference therebetween. From these facts, it is apparent that between adjacent ones of the group of substantial hyperbolas disposed with the above-described interval therebetween, there exists a constant phase difference with respect to the spatial modulation in the direction of substantial ellipses orthogonal thereto. Hence, with the constant phase difference, modulation is applied, between sampling points located on the same substantial ellipse and located at intersections with adjacent substantial hyperbolas, along the direction of the ellipse. The same applies to the group of substantial ellipses disposed with a similar interval therebetween. Hence, the adjacent sampling points thus defined are allocated in the hyperbola direction and the ellipse direction with the constant phase difference in modulation. Using Formula (6) and Formula (7), sampling is performed with the same phase interval upon detecting velocity components in the respective directions, thereby simplifying the calculation procedure.

It is particularly preferable that this phase difference is n/m, where m is an integer. In this case, adjacent substantial hyperbolas and adjacent substantial ellipses have a relation in phase with a cycle of m. As integer m is larger, the number of sampling is increased to result in large load in the process. However, precision is also increased in detecting a displacement. Particularly, m≧4 is preferable.

This condition can be expressed in the different way using Formula (4) as follows. That is, the two groups of curves for determining the sampling points are defined such that: the group of hyperbolas is a set of curves or straight lines selected so that a difference between times taken for ultrasonic pulses to reach from the two apexes or centroids in the apodization with two peaks is substantially the same, the difference between the times taken for the ultrasonic pulses to reach from the two points is different in value between adjacent curves or adjacent straight lines by 1/m of the wavelength of each ultrasonic wave used; the group of ellipses is a group of curves selected so that a total of the times taken for the ultrasonic pulses to reach from the two points is substantially the same, and the total of times taken for the ultrasonic pulses to reach from the two points is different between adjacent curves by 1/n of the wavelength of the ultrasonic wave used.

It should be noted that each of m and n is an integer, and is preferably 4 or greater.

In particular, with m=4 and n=4, velocities in the ellipse direction and the hyperbola direction can be found using Formula (9) and Formula (10). Using the relation of Formula (2) therefor, displacements in the ellipse direction and the hyperbola direction can be found.

The following describes an exemplary method for allocating the sampling points with such an equal phase difference, with reference to FIG. 2.

Assuming that the interval between the two focal points is d=2f, a coordinate origin O is taken at a midpoint between the two focal points and the coordinates of the two focal points are taken as (−f, 0) and (f, 0). As described above, a hyperbola is determined by a difference 2ρ between distances to the two focal points, and an ellipse is determined by a total S of distances to the two focal points. This is slightly modified to determine a hyperbola parameter u and an ellipse parameter v as follows:

[Formula 11]

$$u = \rho \quad (11\text{-}1)$$

$$v = S - f \quad (11\text{-}2)$$

Hyperbolas and ellipses determined by hyperbola parameter u and ellipse parameter v on this occasion are as illustrated by FIG. 2(a) and FIG. 2(b) respectively. Further, an orthogonal coordinates (x, y) can be expressed using hyperbola parameter u and ellipse parameter v as follows:

[Formula 12]

$$(x, y) = \left( \frac{u(v+f)}{f}, \frac{\sqrt{(v^2 + 2vf)(f^2 - u^2)}}{f} \right), \quad (12)$$

$$(-f \leq u \leq f, 0 \leq v < \infty)$$

In order to obtain a constant interval between the totals of the distances from the two focal points and a constant interval between differences thereof, it is convenient to determine an interval between hyperbolas or ellipses using an acoustic velocity c for common sampling time interval T. In this case, a point $Q_{ij}$ designated by a hyperbola index i and an ellipse index j (i=0, ±1, ±2, ..., and j=1, 2, 3, ...) is illustrated in FIG. 2(c). Further, point $Q_{ij}$, represented as $(x_{ij}, y_{ij})$ in orthogonal coordinates, can be expressed as follows:

[Formula 13]

$$u = \frac{1}{2}cTi \qquad (13\text{-}1)$$

$$v = \frac{1}{2}cTj \qquad (13\text{-}2)$$

$$(x_{ij}, y_{ij}) = \left( \frac{\frac{1}{2}cTi\left(\frac{1}{2}cTj + f\right)}{f}, \frac{\sqrt{\left(\left(\frac{1}{2}cTj\right)^2 + cTjf\right)\left(f^2 - \left(\frac{1}{2}cTi\right)^2\right)}}{f} \right) \qquad (13\text{-}3)$$

Further, for similarity to a steering operation performed in normal beam forming, hyperbola index i will be referred to as "line number" and ellipse index j will be referred to as "in-line sample number".

First Embodiment

The present embodiment relates to a device (system) for finding two-dimensional displacement distributions before and after applying pressure to a subject, so as to measure a two-dimensional strain distribution.

Figure 3:
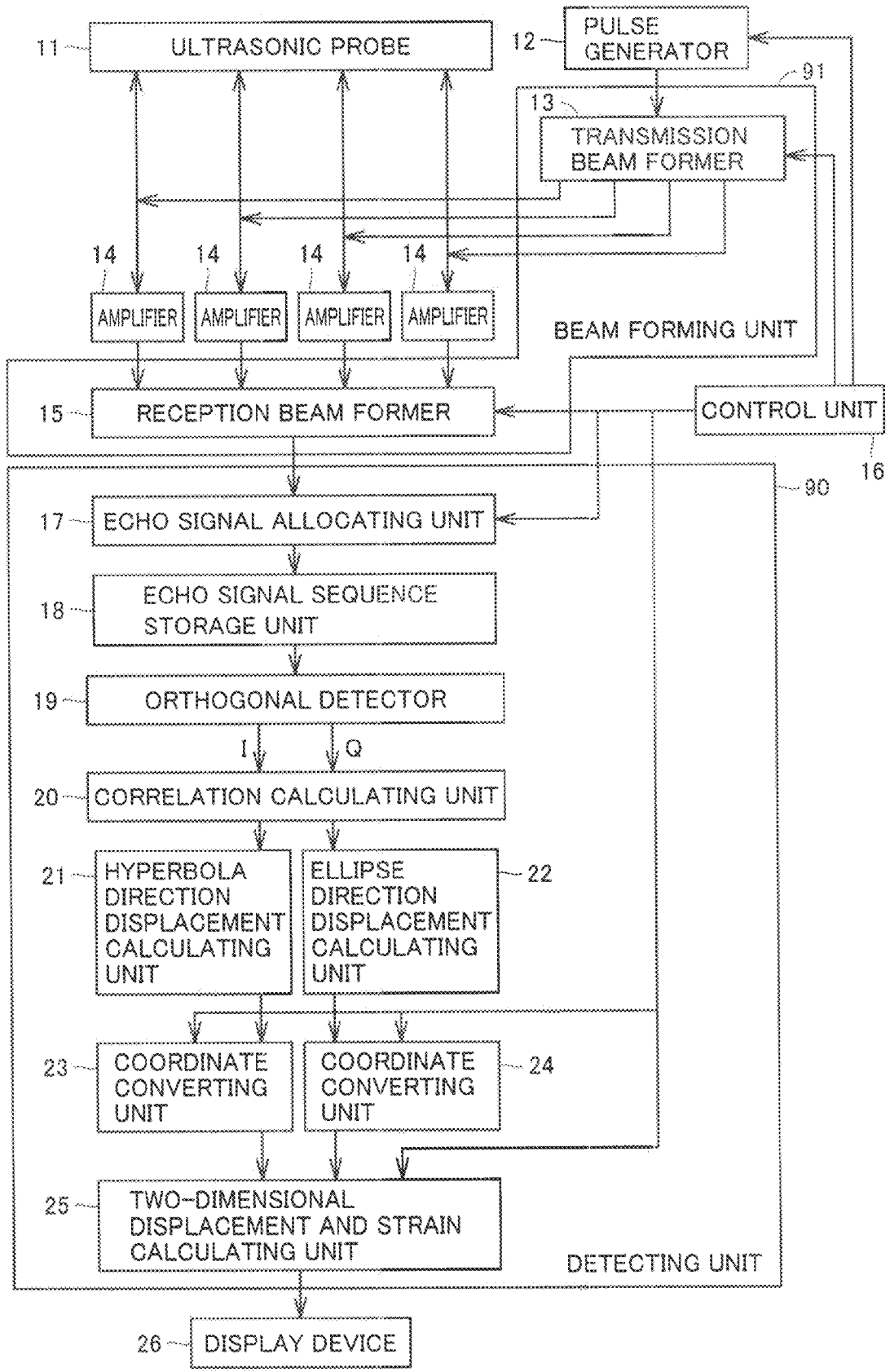
FIG. 3 shows a preferable embodiment of the present invention.

FIG. 3 shows a configuration of the present embodiment.

An ultrasonic diagnostic device (system) in FIG. 3 includes an ultrasonic probe 11, a pulse generator 12, a transmission beam former 13, amplifiers 14, a control unit 16, a reception beam former 15, a detecting unit 90, and a display device 26. Transmission beam former 13 and reception beam former 15 constitute a beam forming unit 91.

Detecting unit 90 includes an echo signal allocating unit 17, an echo signal sequence storage unit 18, an orthogonal detector 19, a correlation calculating unit 20, a hyperbola direction displacement calculating unit 21, an ellipse direction displacement calculating unit 22, a coordinate converting unit 23, a coordinate converting unit 24, and a two-dimensional displacement and strain distribution calculating unit 25.

Ultrasonic probe 11 is constituted by a transducer element array. Each transducer element transmits an ultrasonic wave into the subject and receives reflected wave thereof.

Pulse generator 12 generates a transmission pulse in response to a transmission trigger from control unit 16.

Control unit 16 stores a sampling point information table in which the arrangement of sampling points shown in FIG. 2(c) and location information thereof are described. For each transmission pulse, control unit 16 sets, to transmission beam former 13 and reception beam former 15, an amount of delay for each transducer element so as to focus a transmission ultrasonic wave on a sampling point $Q_{ij}$ along a line number i.

Figure 4:
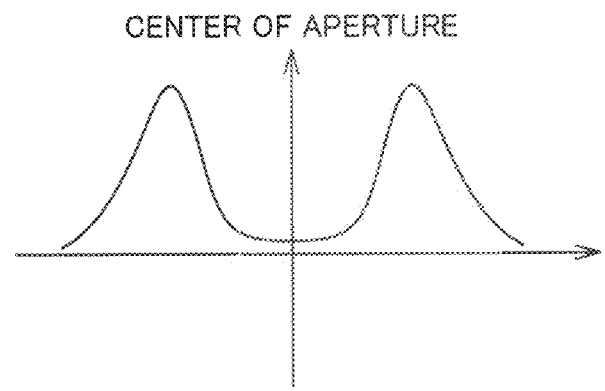
FIG. 4 shows apodization in the embodiment of the present invention.

The transmission pulse generated by pulse generator 12 is delayed by the amount of delay set by transmission beam former 13, and drives each transducer element of the transducer element array of ultrasonic probe 11 with a driving voltage adjusted to have an amplitude with transmit apodization as shown in FIG. 4. The ultrasonic wave to be transmitted from ultrasonic probe 11 is spatially modulated by the apodization with two peaks shown in FIG. 4 as described above, and is focused for transmission by the delay provided by transmission beam former 13, thus being converged to a target sampling point $Q_{ij}$.

Reflected echo signals reflected in the vicinity of sampling point $Q_{ij}$ are received by ultrasonic probe 11 and the reception signals, sent from the transducer elements, are amplified by amplifiers 14. In a more preferable embodiment, each amplifier 14 includes an AD (Analog to Digital) converter to convert each reception signal into a digital signal.

The digital reception signal from each transducer element is delayed by reception beam former 15 by an amount of delay set for each transducer element, is provided with the receive apodization with two peaks as shown in FIG. 4, and is thereafter added (phased and added) for each transducer element. The signal thus phased and added has an increased reception sensitivity around target sampling point $Q_{ij}$. At the same time, the signal thus phased and added has become a reception echo signal two-dimensionally spatially modulated for the reception sensitivity by the receive apodization with two peaks, and is output from reception beam former 15.

The reception echo signal thus output is sent to echo signal allocating unit 17. Echo signal allocating unit 17 extracts data having an appropriate length and including an echo signal for the vicinity of target sampling point $Q_{ij}$, based on the location information of target sampling point $Q_{ij}$ of control unit 16. Then, echo signal allocating unit 17 stores it in a corresponding portion of echo signal sequence storage unit 18. The length of the data thus extracted may include only an echo signal value for the point $Q_{ij}$ to reduce a data storage region, but may include values for a plurality of sampled points including point $Q_{ij}$ and coming before and after point $Q_{ij}$. In this case, the data length and the order of storing a value of sampling point $Q_{ij}$ in the data preferably correspond to each other.

As a result, in echo signal sequence storage unit 18, corresponding echo data are allocated in accordance with the order of the line numbers and the order of the distances to the ultrasonic probe. For example, echo reception data corresponding to sampling points Q-m, 1; Q-m, 2; ..., Q-m+1, 1; Q-m+1, 2; ... shown in FIG. 2(c) are stored in accordance with the order of line numbers and the order as to how closer they are to the ultrasonic probe. FIG. 2(c) illustrates a case where m=1.

Figure 5:
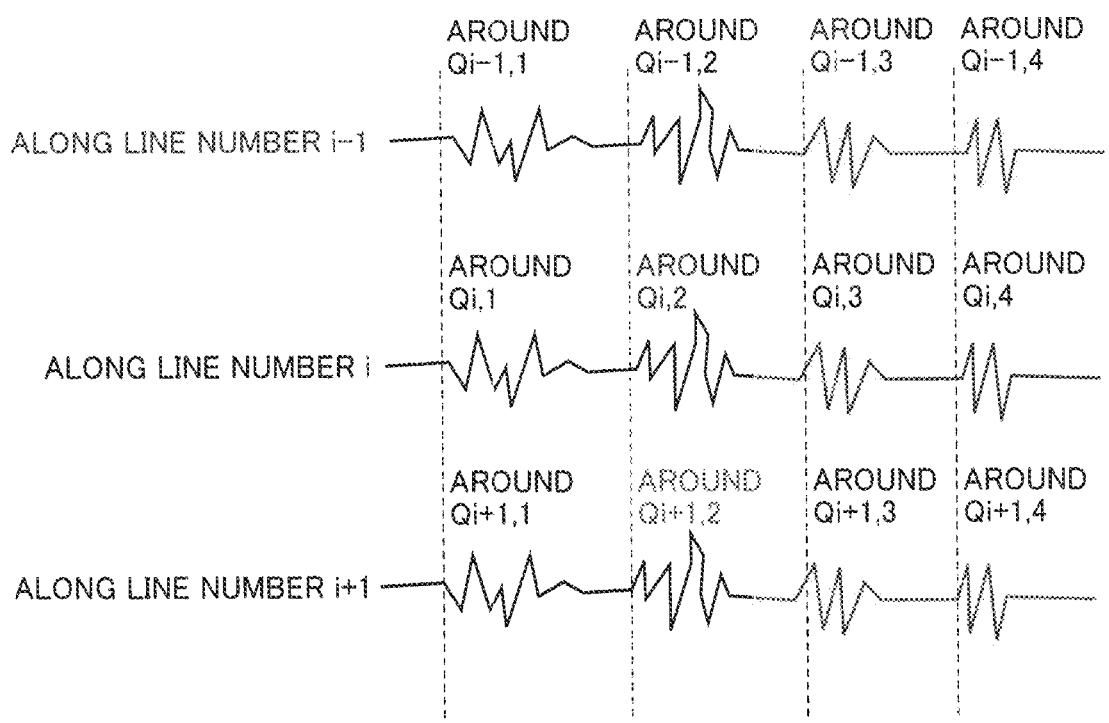
FIG. 5 shows echo reception signals in the embodiment of the present invention.

FIG. 5 shows a schematic view of the echo reception signals stored in this way.

Control unit 16 obtains, for example, echo data in the order of sampling points Q-m, 1; Q-m, 2, ... Q-m+1, 1; Q-m+1, 2; ... in accordance with the sequence of sampling points described in the sampling point information table. Control unit 16 prepares amounts of delay for transmission focusing and reception focusing in accordance with the order described in the sampling point information table, based on the location information of the corresponding sampling points. After setting the amounts of delay for transmission beam former 13 and reception beam former 15 respectively, a transmission trigger is sent to pulse generator 12. Thereafter, as described above, in accordance with the transmission trigger, pulse generator 12 generates a transmission pulse, which is then delayed and apodized by transmission beam former 13. Then, ultrasonic probe 11 transmits an ultrasonic wave focused on a predetermined sampling point, and receives an echo thereof. The reception signal is amplified and digitalized by each amplifier 14, and then is phased and added by reception beam former 15 to generate a reception echo signal.

In accordance with the sampling point information table of control unit 16, echo signal allocating unit 17 extracts a corresponding portion of the reception echo signal based on the location relation of the desired sampling point, and stores it in a predetermined portion of echo signal sequence storage unit 18. Based on the sampling point information table, control unit 16 repeats the above-described procedure to obtain, in echo signal sequence storage unit 18, reception echo signals for sampling points $Q_{ij}$ over the entire measurement area.

As a result, as shown in FIG. 5, a series of echo signal sequences are obtained for specific line numbers. The echo signal sequences correspond to reception echo signals along substantial hyperbolas corresponding to line numbers i=0, ±1, ±2, . . . as shown in FIG. 2(c). Further, a set of echo signal sequences for all the line numbers in the entire measurement area constitutes one frame data.

The echo signal sequences for the line numbers may be stored in series throughout the frame data. However, preferably, as schematically shown in FIG. 5, the echo signal sequences for the line numbers are arranged in parallel, and data can be read out therefrom such that when a line number is designated, values of echo signals for the line can be read in order of time sampling, and such that when a sampling number is designated on a line, values of echo signals for the sampling number are read in order of line numbers. The data of echo signal sequences obtained when designating the line number in this way is termed "line echo signal data" or "scan line signal data". On the other hand, the sequence of signal data obtained when designating the sampling number on the line is termed as "line intersection echo signal data" or "scan line orthogonal signal data". In conjunction with FIG. 2(c), the line echo signal data corresponds to a value of an echo signal from a point located on and along a substantial hyperbola, whereas the line intersection echo signal data corresponds to a value of an echo signal from a point located on and along a substantial ellipse.

Further, in the case where not only the echo signal value for sampling point $Q_{ij}$ but also the echo signal values for the plurality of points including sampling point $Q_{ij}$ and located in the vicinity of sampling point $Q_{ij}$ are stored as the data in echo signal sequence storage unit 18, it may be configured to read data such that data sets of echo signal values for the plurality of points can be read in order of the line numbers in response to designation of a sampling number on a line. The series of data sets are referred to as "line intersection echo signal set data".

In order to measure a two-dimensional strain distribution for external pressure application, frame data is first sampled before the pressure application in accordance with the procedure above. The frame data thus sampled is stored in echo signal sequence storage unit 18 as pre-pressure application frame data. Thereafter, pressure is applied externally. Frame data obtained during the pressure application is stored therein as post-pressure application frame data. Each of the pre-pressure application frame data and the post-pressure application frame data is constituted by a set of echo signal sequences corresponding to line numbers i=0, ±1, ±2, . . . .

Using the pre-pressure application frame data and the post-pressure application frame data as well as orthogonal detector 19 to two-dimensional displacement and strain distribution calculating unit 25, two-dimensional displacement distributions and strain distributions before and after the pressure application are found.

The following describes an overview of the method for measuring a two-dimensional displacement in the present embodiment.

In the present embodiment, in the vicinity of each sampling point a displacement component in the substantial hyperbola direction and a displacement component in the substantial ellipse direction are found independently.

The line echo signal data for each line number before and after the pressure application are read from echo signal sequence storage unit 18. The line echo signal data correspond to echo signal sequences along a substantial hyperbola in a corresponding line number. Hence, by performing complex correlation arithmetic between the corresponding line echo signal data before the pressure application and the corresponding line echo signal data after the pressure application, a displacement along the substantial hyperbola for the corresponding line number before and after the pressure application can be calculated on the substantial hyperbola.

Further, from echo signal sequence storage unit 18, line intersection echo signal data for each in-line sampling number before and after the pressure application are read out. The line intersection echo signal data correspond to echo signal sequences along a substantial ellipse for a corresponding sampling number. Hence, by performing complex correlation arithmetic between the line intersection echo signal data before the pressure application and the line intersection echo signal data after the pressure application, a displacement along the substantial ellipse for the corresponding sample number before and after the pressure application can be calculated on the substantial ellipse.

For the complex correlation arithmetic, orthogonal detector 19 obtains an analysis signal from each signal sequence of the pre-pressure application frame data and the post-pressure application frame data. The analysis signal is constituted by the original signal, an I signal, and a Q signal having a phase deviated by $\pi/4$ from that of I signal. For generation of the analysis signal, Hilbert transform rather than the orthogonal detection can be employed.

Correlation calculating unit 20 uses the pre-pressure application frame data and the post-pressure application frame data to perform correlation arithmetic between the line echo signal data corresponding to each line number before the pressure application and the line echo signal data corresponding to the line number after the pressure application, and sends a result thereof to hyperbola direction displacement calculating unit 21. Further, correlation calculating unit 20 performs correlation arithmetic between the line intersection echo signal data corresponding to each in-line sample number before the pressure application and the echo signal data corresponding to the in-line sample number after the pressure application. Then, correlation calculating unit 20 sends a result thereof to ellipse direction displacement calculating unit 22.

Hyperbola direction displacement calculating unit 21 utilizes the result of correlation arithmetic sent from correlation calculating unit 20, to find a displacement along the substantial hyperbola for each line number at a sampling point located on the substantial hyperbola. Then, hyperbola direction displacement calculating unit 21 sends a result thereof to coordinate converting unit 23. The arithmetic result of hyperbola direction displacement calculating unit 21 is a value of the displacement along the hyperbola at the sampling point for each line number, and represents a displacement component in the tangential direction of the hyperbola at the sampling point. Coordinate converting unit 23 calculates the tangential direction of the hyperbola extending through each sampling point, calculates a two-dimensional orthogonal coordinate component of the obtained displacement along the hyperbola, and sends it to two-dimensional displacement and strain distribution calculating unit 25. The tangent of the substantial hyperbola extending through each sampling point can be calculated when the sampling point information table is provided, and therefore can be calculated for each sampling point in advance.

Likewise, ellipse direction displacement calculating unit 22 uses the result of correlation arithmetic sent from correlation calculating unit 20, to find a displacement along a substantial ellipse for each in-line sampling number at a sampling point located on the substantial ellipse. Then, ellipse direction displacement calculating unit 22 sends a result thereof to coordinate converting unit 24. Coordinate converting unit 24 calculates a tangential direction of the ellipse extending through each sampling point, calculates a two-dimensional orthogonal coordinate component of the obtained displacement along the ellipse, and sends it to two-dimensional displacement and strain distribution calculating unit 25. The tangent of the substantial ellipse extending through each sampling point can be calculated when the sampling point information table is provided, and therefore can be calculated for each sampling point in advance.

Two-dimensional displacement and strain distribution calculating unit 25 combines the displacement component in the tangential direction of the substantial hyperbola provided from hyperbola direction displacement calculating unit 21, with the displacement component in the tangential direction of the substantial ellipse provided from ellipse direction displacement calculating unit 22, thereby finding an orthogonal coordinate component of a two-dimensional displacement in each sampling point.

Display device 26 displays the found two-dimensional displacement at the location of each sampling point. As the display, for example, the following can be used: vector representation of the two-dimensional displacement at each sampling point, color contour display corresponding to the absolute value of the displacement; or color contour display corresponding to the value of each component in the orthogonal coordinate.

Further, two-dimensional displacement and strain distribution calculating unit 25 finds a strain value from the value of two-dimensional displacement in each sampling point and the location coordinates of the sampling point. The strain can be found by differentiating the displacement with respect to the spatial coordinates. For example, elongation and strain $\sigma_{xx}$, $\sigma_{yy}$ are defined as follows:

[Formula 14]

$$\sigma_{xx} = \frac{\partial(\Delta x)}{\partial x} \tag{14-1}$$

$$\sigma_{yy} = \frac{\partial(\Delta y)}{\partial y} \tag{14-2}$$

Here, $\Delta x$, $\Delta y$ respectively indicate an x direction displacement and a y direction displacement. For approximation of the spatial differentiation for determining the strain from the displacement at the sampling point, various conventional approximation methods can be used. However, in the present embodiment, the sampling point is on an atypical lattice, so differentiation may be, for example, as follows:

[Formula 15]

$$\frac{\partial u(Q_{ij})}{\partial x} \approx \frac{\begin{aligned}&u(Q_{i,j+1})(\Delta y_2 - \Delta y_3) +\\&u(Q_{i+1,j})(\Delta y_3 - \Delta y_1) + u(Q_{i+1,j+1})(\Delta y_1 - \Delta y_2)\end{aligned}}{\begin{aligned}&\Delta x_1(\Delta y_2 - \Delta y_3) +\\&\Delta x_3(\Delta y_3 - \Delta y_1) + \Delta x_3(\Delta y_1 - \Delta y_2)\end{aligned}} \tag{15-1}$$

$$\frac{\partial u(Q_{ij})}{\partial y} \approx \frac{\begin{aligned}&u(Q_{i,j+1})(\Delta x_2 - \Delta x_3) +\\&u(Q_{i+1,j})(\Delta x_3 - \Delta x_1) + u(Q_{i+1,j+1})(\Delta x_1 - \Delta x_2)\end{aligned}}{\begin{aligned}&\Delta y_1(\Delta x_2 - \Delta x_3) +\\&\Delta y_3(\Delta x_3 - \Delta x_1) + \Delta y_3(\Delta x_1 - \Delta x_2)\end{aligned}} \tag{15-2}$$

$$\Delta x_1 = x_{i+1,j} - x_{ij} \tag{15-3}$$

$$\Delta x_2 = x_{i,j+1} - x_{ij} \tag{15-4}$$

$$\Delta x_3 = x_{i+1,j+1} - x_{ij} \tag{15-5}$$

$$\Delta y_1 = y_{i+1,j} - y_{ij} \tag{15-6}$$

$$\Delta y_2 = y_{i,j+1} - y_{ij} \tag{15-7}$$

$$\Delta y_3 = y_{i+1,j+1} - y_{ij} \tag{15-8}$$

Here, $u(Q_{ij})$ indicates an amount of the x direction displacement or the y direction displacement at sampling point $Q_{ij}$. Moreover, $x_{ij}$, $y_{ij}$ respectively represent the x coordinate and the y coordinate of sampling point $Q_{ij}$, and are in relation to each other as indicated in Formula (13).

Similarly, shear strain at the sampling point can be found as follows:

[Formula 16]

$$\sigma_{xy} = \frac{1}{2}\left(\frac{\partial(\Delta x)}{\partial y} + \frac{\partial(\Delta y)}{\partial x}\right) \tag{16}$$

The strain thus determined at the sampling point is displayed on display device 26. For the display, the following can be utilized: color contour display of each strain; two-dimensional vector representation of each component of the elongation and strain; or the like.

The strain value may be calculated using the displacements in the substantial hyperbola direction and the substantial ellipse direction before the coordinate conversion in each of coordinate converting units 22 and 23. In this case, the strain value can be found from differentiation for each direction as the local orthogonal coordinates of the substantial hyperbola direction and substantial ellipse direction. Hence, the spatial differentiation can be simplified. However, when converting it to an amount of strain in normal orthogonal coordinates, metric tensor $g_{ij}$ needs to be calculated for conversion from the curvilinear coordinates.

Further, in the present embodiment, the frame data of two frames before and after the pressure application are used to calculate the cross-correlations between the corresponding line signal data before the pressure application and the corresponding line signal data after the pressure application, as well as between the corresponding line intersection signal data before the pressure application and the corresponding line intersection signal data after the pressure application. However, the two-dimensional displacement distribution and two-dimensional velocity distribution can be measured by increasing the number of times of transmission and reception to produce a larger number of frame data at different times (with an equal time interval $T_p$ therebetween), and calculating cross-correlation between adjacent line signal data and between adjacent line intersection signal data from the frame data of different times, using Formula (9) and Formula (10).

In the present embodiment, particularly, the configurations of ultrasonic probe 11 to reception beam former 15 are similar to those of a conventional ultrasonic diagnostic device.

Hence, components of the conventional ultrasonic diagnostic device can be utilized in adding the function of measuring a two-dimensional displacement, advantageously. Further, the functions of echo signal allocating unit 17 to two-dimensional displacement and strain distribution calculating unit 25 can be implemented by a program on a general-purpose PC.

Second Embodiment

In the first embodiment, when the number of sampling points is increased to improve spatial resolution for the two-dimensional displacement distribution, it takes a longer time until the displacement distribution is displayed because transmission/reception need to be done for all the sampling points. In the present embodiment, all the reception signal data are stored which are received by the transducer elements of the ultrasonic probe in response to sequential transmission from the transducer elements of the transducer element array. In accordance with the data thus stored, beam forming is performed by means of calculation to form a beam conforming to the substantial hyperbola. Accordingly, an echo reception signal sequence conforming to the substantial hyperbola is formed.

In other words, this embodiment provides an example characterized in that the ultrasonic probe focuses the ultrasonic wave by aperture synthesis achieved by ultrasonic transmission by at least one or more of the group of ultrasonic transducer elements and reception by ultrasonic transducer elements more in number than the ultrasonic transducer elements that transmit.

In the present embodiment, after performing transmission for the number of times corresponding to the number of the transducer elements of the transducer element array, a process is performed with calculation, thereby improving spatial resolution. Hence, even when the number of sampling points is increased, operation speed for displaying two-dimensional displacement distribution becomes relatively faster than that in the first embodiment, advantageously.

Figure 6:
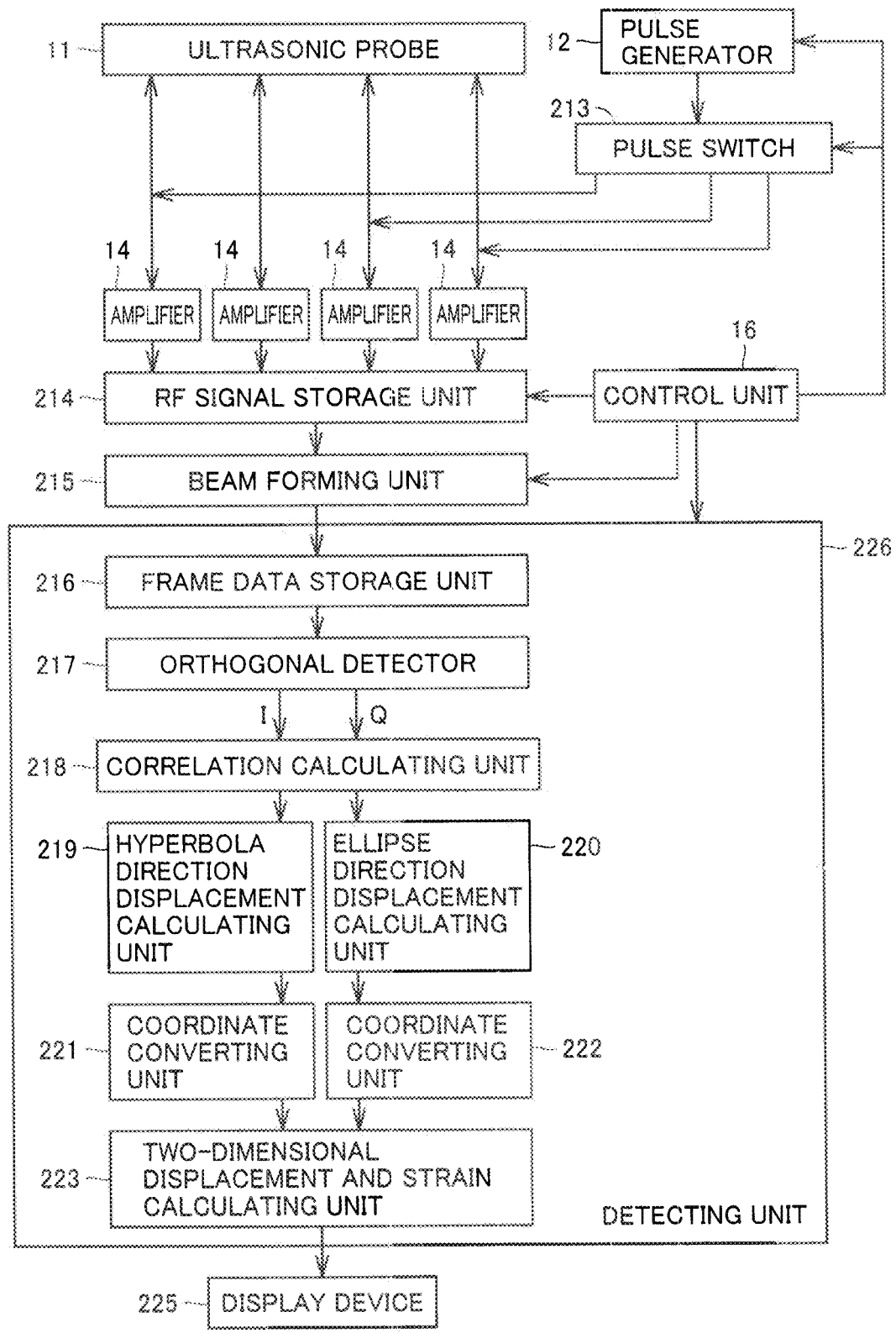
FIG. 6 shows another preferable embodiment of the present invention.

FIG. 6 shows a configuration of the present embodiment. It should be noted that the same members as those in FIG. 3 are indicated by the same reference characters.

The ultrasonic diagnostic device (system) in FIG. 6 includes an ultrasonic probe 11, a pulse generator 12, a pulse switch 213, amplifiers 14, a control unit 16, an RF signal storage unit 214, a beam forming unit 215, a detecting unit 226, and a display device 225.

Ultrasonic probe 11 is constituted by a transducer element array. Each transducer element transmits an ultrasonic wave into a subject and receives reflected wave thereof.

Pulse generator 12 generates a transmission pulse in response to a transmission trigger from control unit 16. Pulse switch 213 switches between transmission pulses to be sent to the transducer elements of the transducer element array of ultrasonic probe 11, in accordance with a control signal from control unit 16.

From one transducer element of the transducer element array of ultrasonic probe 11, an ultrasonic wave is transmitted. Ultrasonic echo corresponding to the ultrasonic wave is received by all the transducer elements of the transducer element array of ultrasonic probe 11.

The reception signals from all the transducer elements of the transducer element array are amplified by amplifiers 14. Each of amplifiers 14 preferably has an AD converter to digitalize the reception signal. The digital reception signal from each transducer element is stored in RF signal storage unit 214.

Control unit 16 causes pulse generator 12 to generate a transmission pulse, switches among the transducer elements of the transducer element array to repeat transmission by one transducer element, and causes RF signal storage unit 214 to store therein all the reception signals corresponding to the transmission from the transducer element. This is repeated. Sets of reception signals corresponding to transmissions from all the transducer elements in the transducer element array are stored in RF signal storage unit 214.

Beam forming unit 215 and detecting unit 226 perform beam forming by calculation using the sets of reception signal data stored in RF signal storage unit 214, so as to produce echo reception data sequences conforming to the substantial hyperbolas and echo signal data sequences conforming to the substantial ellipses. Using them, beam forming unit 215 and detecting unit 226 calculate the two-dimensional displacement distribution. Each of beam forming unit 215 and detecting unit 226 is constituted by a general PC (Personal Computer) and can perform the process using software executed thereon, but can be constituted by a dedicated electronic device. Each element in beam forming unit 215 and detecting unit 226 may be constituted by such a dedicated device, but may be a processing constituent unit on software.

Detecting unit 226 includes a frame data storage unit 216, an orthogonal detector 217, a correlation calculating unit 218, a hyperbola direction displacement calculating unit 219, an ellipse direction displacement calculating unit 220, a coordinate converting unit 221, a coordinate converting unit 222, and a two-dimensional displacement and strain distribution calculating unit 223.

Beam forming unit 215 performs beam forming by calculation using the sets of reception signal data stored in RF signal storage unit 214.

The following describes the calculation beam forming.

A transmission pulse signal is represented by $S_0(tk)$. Here, tk represents time of the transmission pulse in digital sense. Assuming that the transmission pulse length is Lt, $S_0(tk)$ is 0 unless 0<tk<Lt. It is assumed that a specific transducer element μ transmits an ultrasonic wave, which is reflected at point P and is then received by a transducer element ν as described above. Due to a propagation delay (the same as P1, P4) by the propagation of the ultrasonic wave, a reception signal $S_{\mu\nu}$ (tn) obtained on this occasion is as follows:

[Formula 17]

$$S_{\mu\nu}(t_m) \sim S_0(t_m - \tau_{\mu\nu}(p)) \quad (17\text{-}1)$$

$$\tau_{\mu\nu}(p) = \frac{d_\mu(p) + d_\nu(p)}{c} \quad (17\text{-}2)$$

Here, $d_\mu(p)$ represents a distance from transmission transducer element μ to point P. Further, $d_\nu(p)$ represents a distance from reception transducer element ν to point P. Furthermore, c represents an acoustic velocity.

Now, assume that the sampling points are arranged as shown in FIG. 2(c), and echo signals are obtained from sampling points $Q_{i1}, Q_{i2}, Q_{i3}, \ldots$ along a certain line number i. In order to two-dimensionally modulate reception sensitivity, an effect of apodization such as the one shown in FIG. 4 is provided. To obtain a reception signal focused on a sampling point $Q_{ij}$, a delay corresponding to the above-described propagation delay is provided. Hence, the following is to be satisfied:

[Formula 18]

$$\hat{S}_h(t_m; Q_{ij}) = \sum_{\mu\nu} a^{(T)}{}_\mu a^{(R)}{}_\nu S_{\mu\nu}\left(t_m + \tau_{\mu\nu}(Q_{ij}) - \frac{\Lambda_h^{(i)}(Q_{ij})}{c}\right) \quad (18)$$

Here, $S_{\mu\nu}$ represents the reception signal data received by transducer element ν in response to the transmission from transducer element μ. Further, $a^{(T)}\mu$ represents a transmit apodization coefficient of transducer element μ, and is varied according to the location of transducer element μ as shown in FIG. 4. Furthermore, $a^{(R)}\nu$ represents a receive apodization coefficient of transducer element ν, and is varied according to the location of transducer element ν as shown in FIG. 4. Moreover, $\Lambda_h(Q_{ij})$ represents a distance from the transmission surface of the ultrasonic probe to sampling point $Q_{ij}$, which is measured along the hyperbola of line number i.

More preferably, to obtain an echo signal from a vicinity of sampling point $Q_{ij}$, a window function W(t) is applied. W(t) has a value different from 0 with time (step) width as long as the transmission pulse length where W(0)=1. For example, a Gaussian distribution of the width of the transmission pulse length may be used.

[Formula 19]

$$\hat{S}_h(t_m; Q_{ij}) = \sum_{\mu\nu} a^{(T)}{}_\mu a^{(R)}{}_\nu S_{\mu\nu}\left(t_m + \tau_{\mu\nu}(Q_{ij}) - \frac{\Lambda_h^{(i)}(Q_{ij})}{c}\right)$$
$$W\left(t_m + \tau_{\mu\nu}(Q_{ij}) - \frac{\Lambda_h^{(i)}(Q_{ij})}{c} - \frac{Lt}{2}\right) \quad (19)$$

To obtain a line echo signal sequence $S_h^{(i)}$ along line number i, echo signals from all the sampling points $Q_{i1}$, $Q_{i2}$, $Q_{i3}$, . . . along line number i may be added together.

[Formula 20]

$$\hat{S}_h^{(i)}(t_m) = \sum_j \hat{S}_h(t_m; Q_{ij}) \quad (20)$$

Similarly, a line intersection echo signal sequence $S_e^{(j)}$ along an in-line sample number j is as follows:

[Formula 21]

$$\hat{S}_e(t_m; Q_{ij}) = \sum_{\mu\nu} a^{(T)}{}_\mu a^{(R)}{}_\nu S_{\mu\nu}\left(t_m + \tau_{\mu\nu}(Q_{ij}) - \frac{\Lambda_e^{(j)}(Q_{ij})}{c}\right) \quad (21\text{-}1)$$

$$\hat{S}_e^{(j)}(t_m) = \sum_i \hat{S}_e(t_m; Q_{ij}) \quad (21\text{-}2)$$

Here, $\Lambda_e^{(j)}(Q_{ij})$ represents a distance from the transmission surface of the ultrasonic probe to sampling point $Q_{ij}$, which is measured along the ellipse of in-line sample number j.

In the present embodiment, by performing the calculation beam forming, line echo signal sequence $S_h^{(i)}$ conforming to the substantial hyperbola of line number i and line intersection echo signal sequence $S_e^{(j)}$ conforming to the substantial ellipse of in-line sample number j can be directly calculated. Line echo signal sequence $S_h^{(i)}$ for each line number, and line intersection echo signal sequence $S_e^{(j)}$ for each in-line sample number j are stored in frame data storage unit 216 as frame data.

As with the first embodiment, in order to measure the two-dimensional displacement before and after pressure application, a series of transmission/reception is first performed before the pressure application to produce pre-pressure application frame data, which is then stored in frame data storage unit 216. Next, pressure is externally applied, and a series of transmission/reception is performed to produce post-pressure application frame data, which is then stored in frame data storage unit 216.

For complex correlation arithmetic, orthogonal detector 217 obtains an analysis signal from each signal sequence of the pre-pressure application frame data and the post-pressure application frame data. The analysis signal is constituted by the original signal, an I signal, and a Q signal having a phase deviated by π/4 from that of I signal. For generation of the analysis signal, Hilbert transform rather than the orthogonal detection can be employed.

Correlation calculating unit 218 uses the pre-pressure application frame data and the post-pressure application frame data to perform correlation arithmetic between line echo signal data $S_h$ corresponding to each line number before the pressure application and line echo signal data $S_h$ corresponding to each line number after the pressure application, and sends a result thereof to hyperbola direction displacement calculating unit 219. Further, correlation calculating unit 218 performs correlation arithmetic between the line intersection echo signal data corresponding to each in-line sample number before the pressure application and the line intersection echo signal data corresponding to each in-line sample number after the pressure application.

Hyperbola direction displacement calculating unit 219 utilizes the result of correlation arithmetic sent from correlation calculating unit 218, to find a displacement along the substantial hyperbola for each line number at each sampling point located on the substantial hyperbola. Coordinate converting unit 221 calculates and outputs a two-dimensional orthogonal coordinate component of the obtained displacement along the hyperbola.

Likewise, ellipse direction displacement calculating unit 220 utilizes the result of correlation arithmetic sent from correlation calculating unit 218, to find a displacement along the substantial ellipse of the sampling number of each line at each sampling point located on the substantial ellipse. Coordinate converting unit 222 calculates and outputs a two-dimensional orthogonal coordinate component of the obtained displacement along the ellipse.

Two-dimensional displacement and strain distribution calculating unit 223 combines the displacement component in the tangential direction of the substantial hyperbola provided from hyperbola direction displacement calculating unit 219, with the displacement component in the tangential direction of the substantial ellipse provided from ellipse direction displacement calculating unit 220, thereby finding an orthogonal coordinate component of the two-dimensional displacement in each sampling point.

Display device 225 displays the found two-dimensional displacement at the location of each sampling point. As the display, the following can be used, for example: vector representation of the two-dimensional displacement at each sampling point; color contour display corresponding to the absolute value of the displacement; or color contour display corresponding to the value of each component in the orthogonal coordinate.

As with the first embodiment, strain resulting from the pressure application can be measured and displayed on display device 225, apparently.

Further, as with the first embodiment, the two-dimensional displacement distribution and two-dimensional velocity distribution can be measured by producing a larger number of frame data at different times (with an equal time interval $T_p$), and calculating cross-correlation between adjacent line signal data and between adjacent line intersection signal data from the frame data of different times, using Formula (9) and Formula (10).

In the present embodiment, only one transducer element of the transducer element array of ultrasonic probe 11 is used for transmission. However, in this case, the transmission ultrasonic wave is decreased in strength, which results in decreased SNR (Signal to Noise Ratio) of the reception signal received by each transducer element of the transducer element array. In order to overcome this disadvantage, a plurality of transducer elements may transmit waves. Meanwhile, the calculation beam forming in the present embodiment is set to transmit a substantially spherical wave (two-dimensionally, concentric circular wave). Hence, when the number of the transmission transducer elements is increased, focus accuracy will be decreased. To address this, the plurality of transmission transducer elements are delayed to effectively generate a spherical wave.

Figure 14:
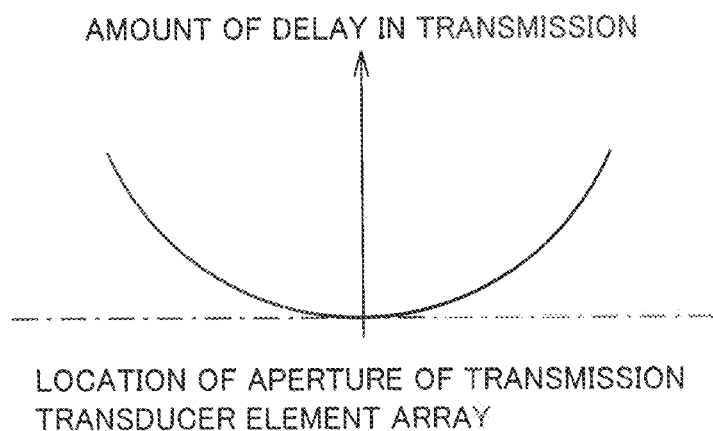
FIG. 14 shows transmission delay in the conventional art.
Figure 15:
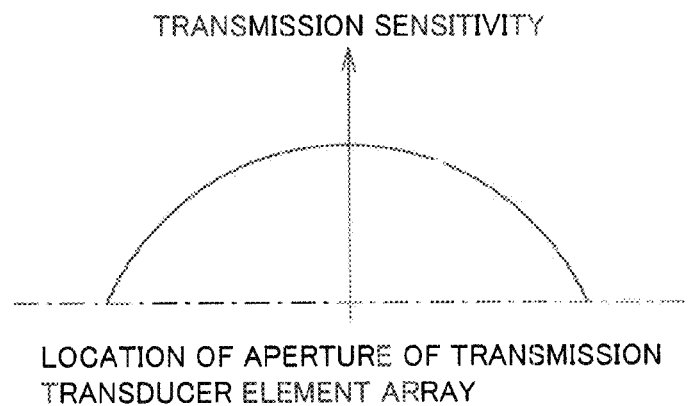
FIG. 15 shows transmit apodization in the conventional art.
Figure 16:
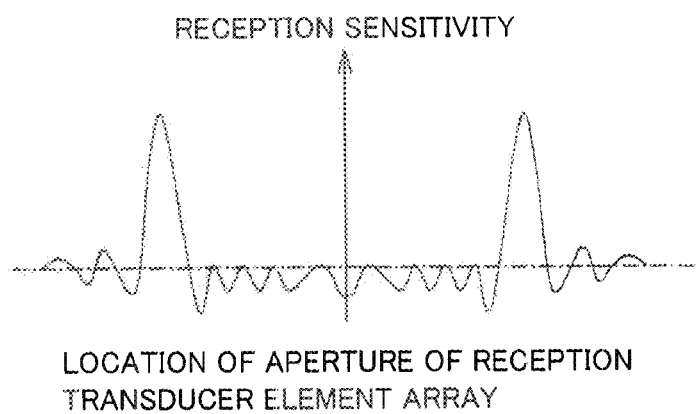
FIG. 16 shows receive apodization in the conventional art.
Figure 17:
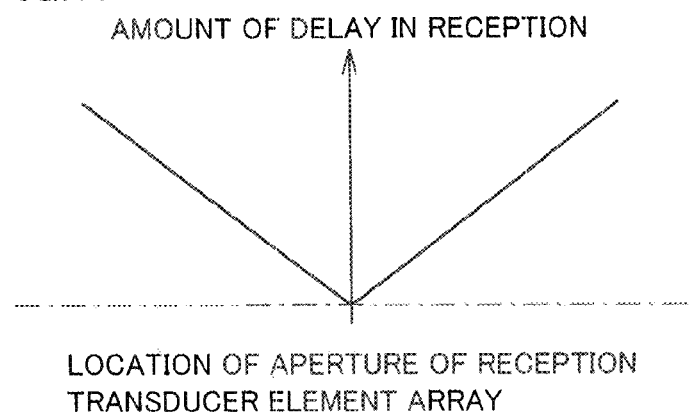
FIG. 17 shows reception delay in the conventional art.
Figure 18:
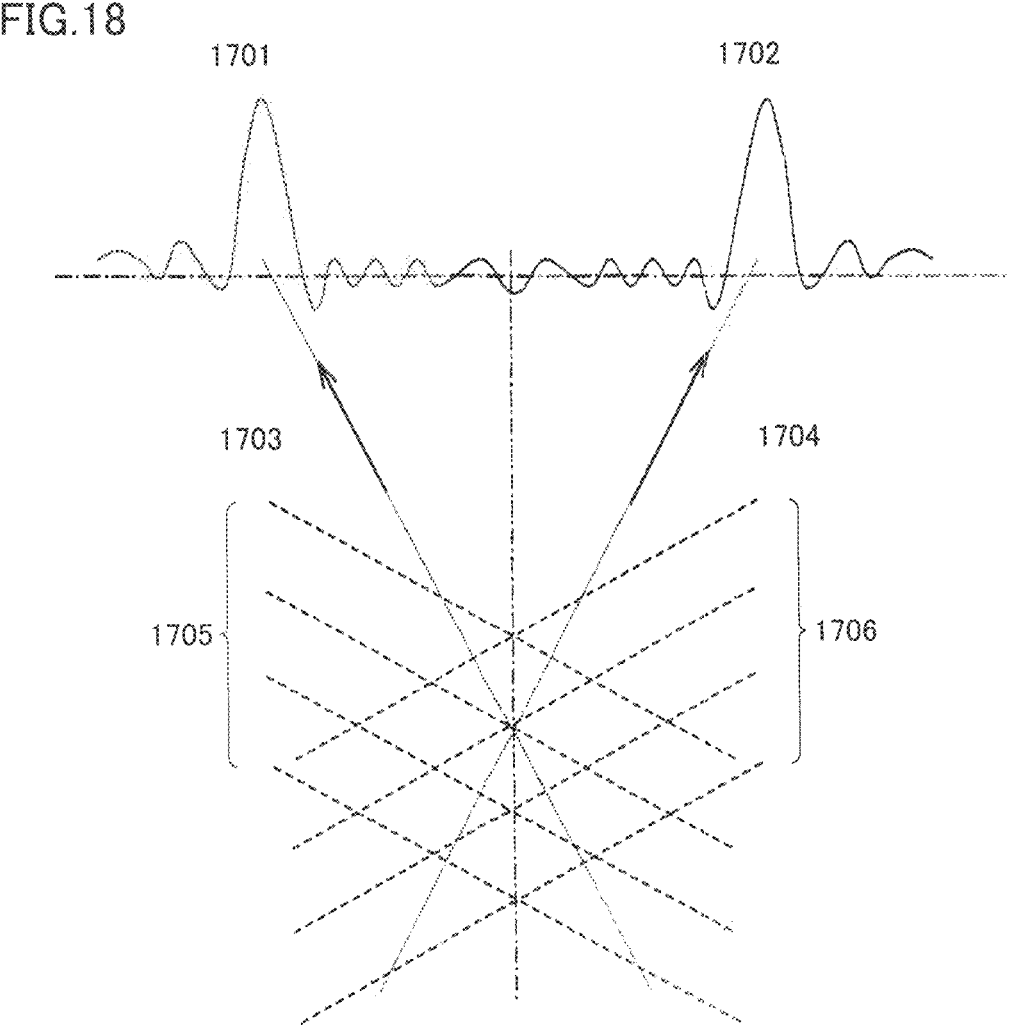
FIG. 18 shows a principle of the conventional art.
Figure 19:
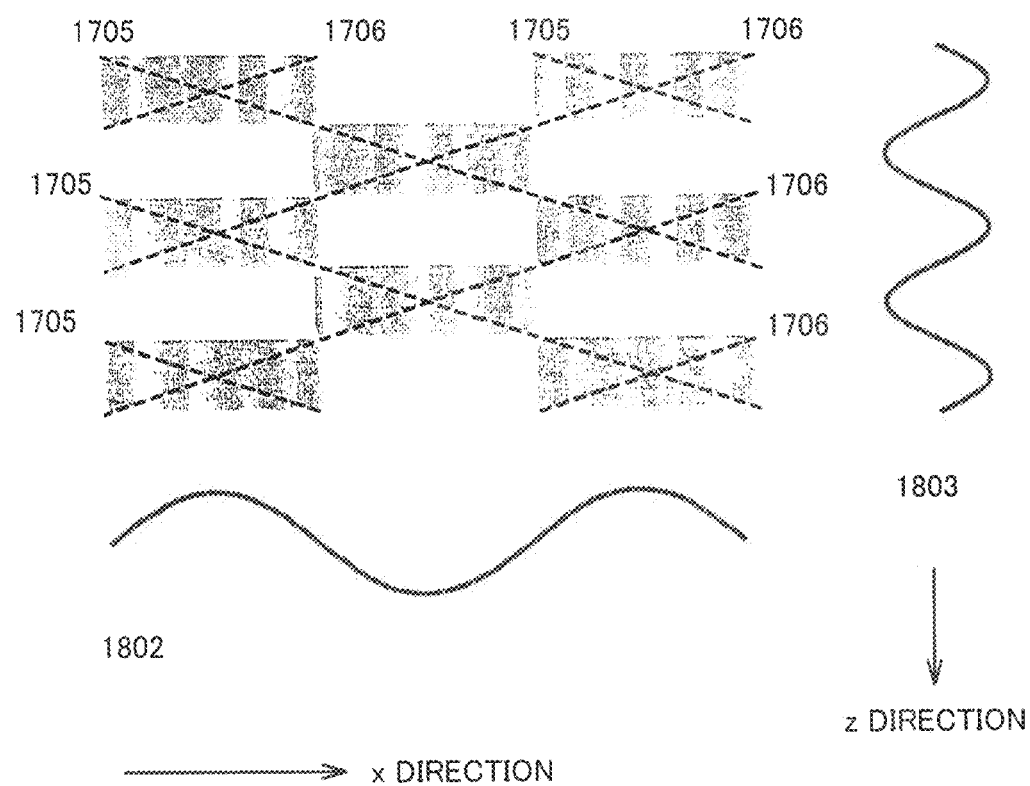
FIG. 19 shows a reception sensitivity distribution in the conventional art.

Referring to FIG. 7, such a transmitting method will be described. Instead of pulse switch 213 shown in FIG. 6, a transmission beam former is used. The transmission beam former selects a plurality of transmission transducer elements 32, which are to transmit, in accordance with control unit 16 and provides each of transmission transducer elements 32 with a delay. The delay thus provided is to form a substantially spherical wave radiated from a virtual wave source 33 at the transducer element array surface or the ultrasonic probe side, unlike the normal delay for transmission focusing to converge the ultrasonic wave. FIG. 7 illustrates an amount of corresponding delay. The delay curve is characterized in that it is vertically symmetrical to that in the case of the normal transmission focusing for convergence as shown in FIG. 14. By such transmission, the substantially spherical wave can be transmitted in a manner similar to that of the transmission using one transducer element as described with reference to FIG. 6. Instead of the operation of sequentially shifting the transducer elements one by one as illustrated in FIG. 6, control unit 16 may change transmission transducer elements 32 and amounts of delay to be applied thereto. In doing so, the calculation beam forming can be performed in a manner similar to that in FIG. 6, using the distance from a corresponding virtual wave source to target sampling point P instead of the distance, $d_\mu(p)$ determined in Formula (17), from transmission transducer element μ to point P.

Accordingly, two or more ultrasonic transducer elements transmit ultrasonic waves, and the ultrasonic waves thus transmitted from the two or more ultrasonic transducer elements are combined to become an spherical wave or effectively cylindrical wave coming from the transmission surface of the group of ultrasonic transducer elements and centered at the virtual sound source assumed at a location opposite to the transmission side. By such transmission, transmission sound pressure is increased to improve SNR, advantageously.

In the present embodiment, the number of times of transmission and reception is determined by the number of the transducer elements of the ultrasonic probe. Hence, even when the number of sampling points is increased to improve the spatial resolution of the two-dimensional displacement distribution, the transmission and reception are not repeated excessively. Accordingly, processing time for spatial resolution can be shorter than that in the first embodiment, advantageously.

(Simulation Result)

The following describes a result of exemplary simulation concerned with two-dimensional displacement distribution measurement calculated from displacement measurement conducted along the substantial hyperbola and displacement measurement conducted along the substantial ellipse based on the embodiment of the present invention.

Explained first is a simulation result of a sensitivity distribution pattern of echo reception signals for point-shaped reflectors. FIG. 8 shows an arrangement in the simulation. A transducer element array 41 corresponding to the ultrasonic probe is illustrated. Point-shaped reflectors 42 serving as a measurement target are illustrated. Point-shaped reflectors 42 are arranged in the form of a cross to face the ultrasonic probe. Using the calculation beam forming method described in the second embodiment, beam focusing conforming to the substantial hyperbola is performed and sampling is performed corresponding to the group of substantial ellipses, so as to calculate echo reception signals. FIG. 9 shows modulation patterns obtained from the echo reception signals at the point scatterer portions in the beam propagating direction and a direction orthogonal thereto.

FIG. 20 shows the reception beam patterns obtained when modulated in a lateral direction with the apodization with two peaks, as described in explaining the problem of the conventional art.

FIG. 9(a) shows a beam pattern in the vicinity of the center of the ultrasonic probe as with FIG. 20(a). FIG. 9(b) shows a beam pattern in the vicinity of an end of the ultrasonic probe as with FIG. 20(b). It is appreciated that by the beam focusing along the substantial hyperbola and the sampling corresponding to the group of substantial ellipses locally orthogonal thereto, echo reception signal data are modulated in an independent direction.

Figure 10:
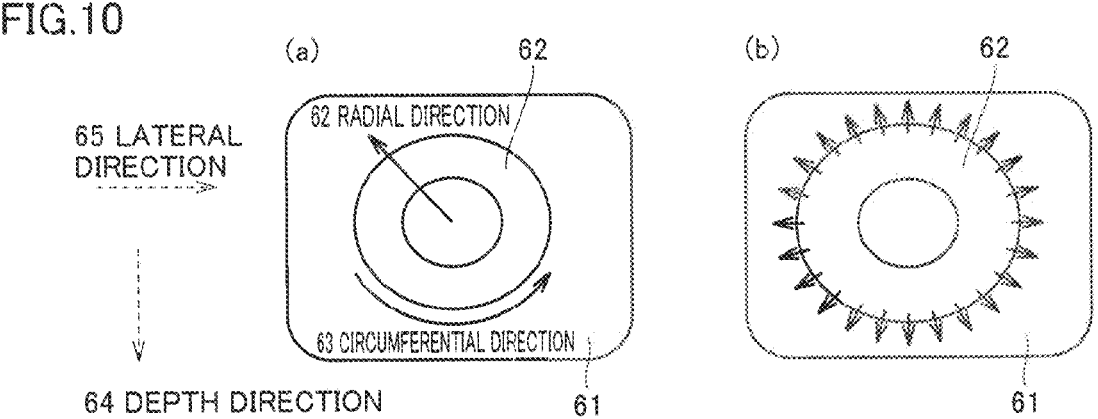
FIG. 10 shows a model of another simulation to illustrate an effect of the embodiment of the present invention.

The following describes a simulation result for the point scatterer using the displacement detecting method based on the embodiment of the present invention. FIG. 10 shows an arrangement in the simulation. A subject model is obtained by arranging a point scatterer region 62 having a high reflectivity (in average) in the manner of a doughnut shaped cross section within a point scatterer region 61 having a low reflectivity (in average). To such a subject model, the calculation beam forming is performed based on the second embodiment, a displacement is measured along the substantial hyperbola, and a displacement is measured in the direction of the substantial ellipse, thereby finding the two-dimensional displacement distribution. The displacements are defined with high reflectivity region 62 being formed at a uniform expansion ratio in a radial direction 62 relative to the center of the doughnut shaped cross section as shown in FIG. 10(b). For ease of description, radial direction 62, a circumferential direction 63, a depth direction 64, and a lateral direction 65 are defined as shown in FIG. 10(a).

Figure 11:
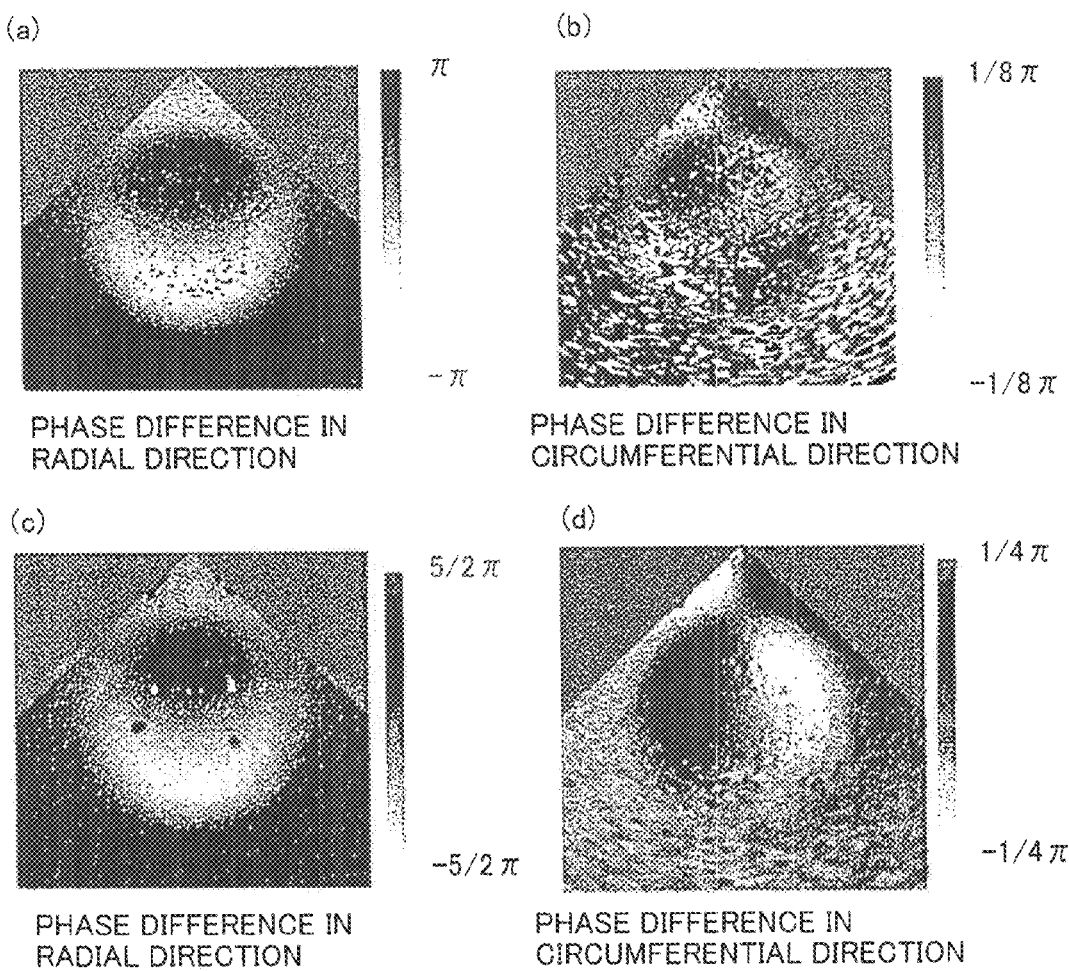
FIG. 11 shows a result of phase calculation simulation by displacement measurement in the embodiment of the present invention.

FIG. 11 shows the two-dimensional displacement distributions obtained by the two-dimensional displacement measurement performed based on the embodiment of the present invention, assuming a phase difference as a unit. For comparison, FIG. 11(a) and FIG. 11(b) respectively show distributions, obtained using the normal Doppler method, in radial direction 62 and circumferential direction 63. From these distributions, it is appreciated that measurement is not attained in the circumferential direction.

Figure 12:
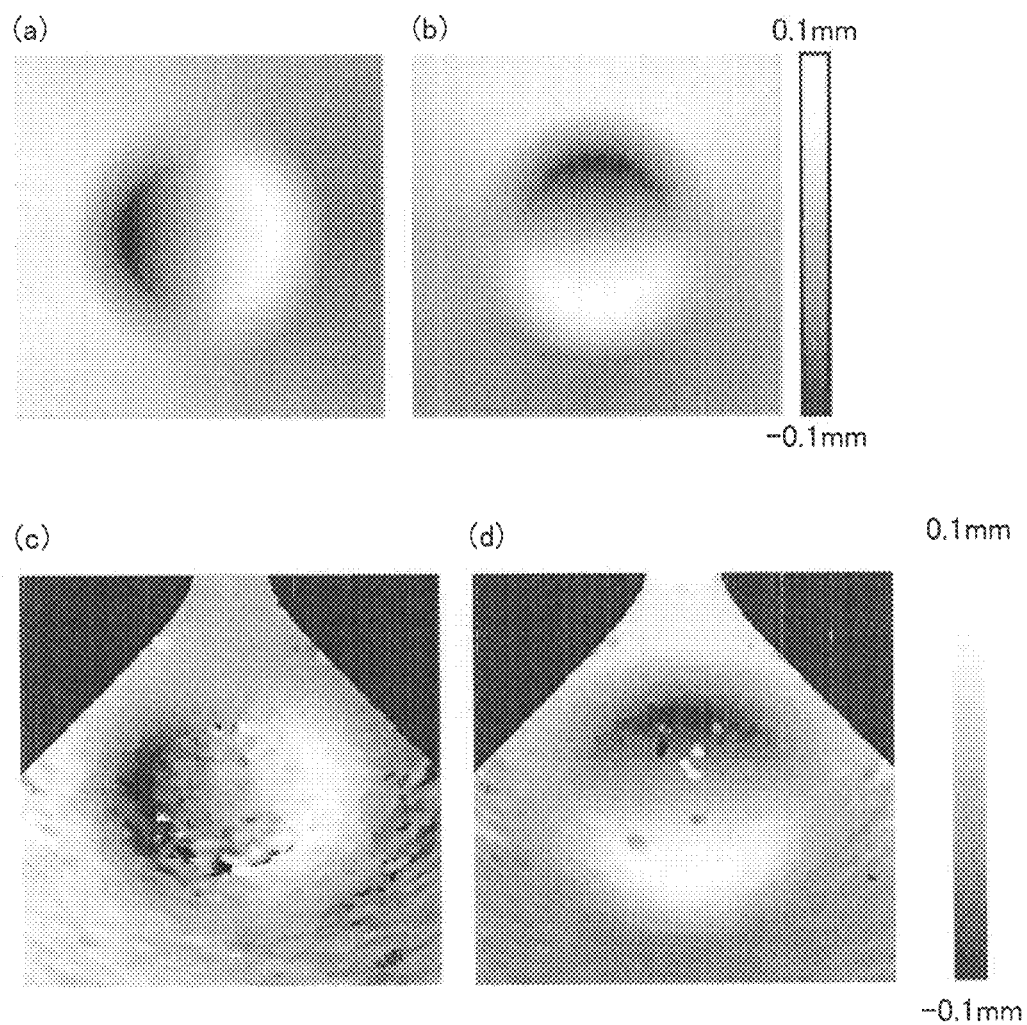
FIG. 12 shows a result of two-dimensional displacement simulation by displacement measurement in the embodiment of the present invention.
Figure 13:
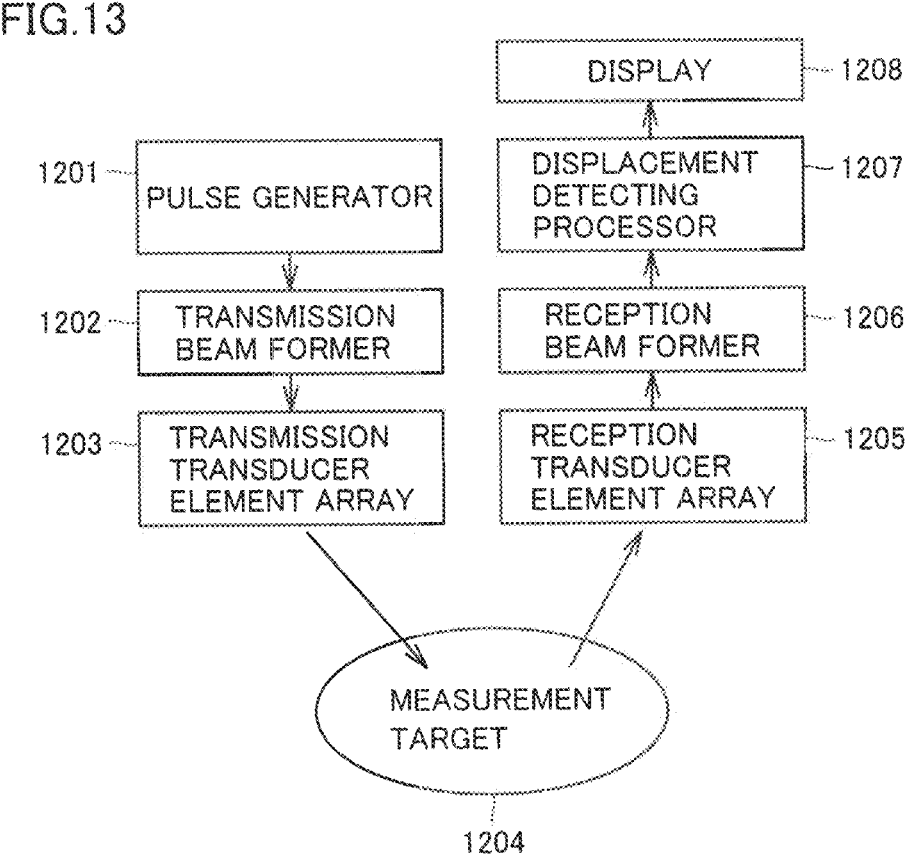
FIG. 13 is a schematic diagram for illustrating a conventional art.

FIG. 11(c) and FIG. 11(d) show distributions obtained by measuring a displacement in the direction along the substantial hyperbola and a displacement in the direction along the substantial ellipse using the present method, and then converting phase differences obtained therefrom into a radial direction 62 component and a circumferential direction 63 component. It is appreciated that the displacement measurement is attained for both the radial direction 62 component and the circumferential direction 63 component. For convenience of normal observation, FIG. 12 shows displacement distributions obtained by converting them into a depth direction 64 component and a lateral direction 65 component. For comparison, FIG. 12(*a*) and FIG. 12(*b*) show actual displacement distributions of the point scatterer of high reflectivity region 62, which are given as a condition for the simulation. FIG. 12(*c*) and FIG. 12(*d*) show simulation results of displacement distributions of the depth direction 64 component and the lateral direction 65 component calculated by the ultrasonic measurement performed based on the embodiment of the present invention. It is appreciated that the given displacement condition is well reproduced.

DESCRIPTION OF THE REFERENCE SIGNS

11: ultrasonic probe; 12, 1201: pulse generator; 13, 1202: transmission beam former; 14: amplifier; 15, 1206: reception beam former; 16: control unit; 17: echo signal allocating unit; 18: echo signal sequence storage unit; 19, 217: orthogonal detector; 20, 218: correlation calculating unit; 21, 219: hyperbola direction displacement calculating unit; 22, 220: ellipse direction displacement calculating unit; 23, 24, 221, 222: coordinate converting unit; 25, 223: two-dimensional displacement and strain calculating unit; 26, 225: display device; 31: transducer element array; 32: transmission transducer element; 33: virtual wave source; 90, 226: detecting unit; 91, 215: beam forming unit; 213: pulse switch; 214: RF signal storage unit; 216: frame data storage unit; 1203: transmission transducer element array; 1204: measurement target; 1205: reception transducer element array; 1207: displacement detecting processor; 1208: display.

The invention claimed is:

1. An ultrasonic diagnostic system comprising:
an ultrasonic probe having a group of ultrasonic transducer elements arranged in at least one direction;
a beam forming unit for forming acoustic field sensitivity modulated in a direction substantially orthogonal to each scan line of a group of scan lines in a subject by focusing an ultrasonic wave on a sequence of sampling points existing along the group of scan lines, and applying delay and apodization to a transmission/reception signal of each of the ultrasonic transducer elements; and
a detecting unit for detecting displacements in at least two directions at each of the sampling points by arithmetic between reception signals for the sampling point at different time points,
wherein said detecting unit detects displacements at the sampling point in a first direction tangential to the scan line that passes through the sampling point, wherein the first direction is tangential to the scan line at the sampling point, and in a second direction tangential to a curve that passes through the sampling point, wherein the second direction is tangential to the curve at the sampling point, and wherein the curve belongs to a group of curves substantially orthogonal to the scan lines,
wherein the group of curves is in the subject, each of the curves is defined by a sequence of points for which a total of times taken for ultrasonic pulses to reach the sequence of points from two fixed points on the ultrasonic probe is substantially the same, and
wherein said group of scan lines are hyperbolas having, as common focal points, the two fixed points on said ultrasonic probe.

2. The ultrasonic diagnostic system according to claim 1, wherein the group of scan lines is selected so that a difference between the times taken for the ultrasonic pulses to reach from the two fixed points is substantially the same, and the difference between the times taken for the ultrasonic pulses to reach from the two fixed points has a constant difference between adjacent curves or adjacent straight lines.

3. The ultrasonic diagnostic system according to claim 1, wherein the sampling points for finding the displacements are arranged on intersections of the group of scan lines and the group of curves substantially orthogonal to the group of scan lines, the group of curves substantially orthogonal to the group of scan lines is a set of curves selected so that a total of the times taken for the ultrasonic pulses to reach from the two fixed points is substantially the same, and the total of the times taken for the ultrasonic pulses to reach the curves from the two fixed points has a constant difference between adjacent curves.

4. The ultrasonic diagnostic system according to claim 1, wherein:
said group of curves substantially orthogonal to the scan lines is a group of ellipses having the two fixed points as common focal points.

5. The ultrasonic diagnostic system according to claim 1, wherein the ultrasonic probe constituted by said group of ultrasonic transducer elements focuses an ultrasonic wave by means of aperture synthesis achieved by transmission of an ultrasonic wave by at least one or more ultrasonic transducer elements of the group of ultrasonic transducer elements, and reception by ultrasonic transducer elements larger in number than the ultrasonic transducer elements that transmit.

6. The ultrasonic diagnostic system according to claim 5, wherein the ultrasonic transducer elements transmitting an ultrasonic wave are two or more ultrasonic transducer elements, and the two or more ultrasonic transducer elements transmit ultrasonic waves such that a sonic wave obtained by combining the ultrasonic waves transmitted from the two or more ultrasonic transducer elements becomes a spherical wave or an effectively cylindrical wave coming from a wave transmission surface of the group of ultrasonic transducer elements and centered at a virtual sound source defined opposite to the wave transmission side.

7. The ultrasonic diagnostic system according to claim 1, wherein said detecting unit has a correlation calculating unit for:
finding a displacement in a direction along said group of scan lines by performing cross-correlation arithmetic between echo signal sequences constituted by echo signal values at a plurality of sampling points along the scan lines at said different time points, and
finding a displacement in a direction along the group of curves substantially orthogonal to said scan lines by performing cross-correlation arithmetic between echo signal sequences constituted by echo signal values at sampling points along the curves substantially orthogonal to the scan lines at said different time points.

8. The ultrasonic diagnostic system according to claim 1, wherein said detecting unit has a correlation calculating unit for:
finding a displacement in a direction along said group of scan lines by performing cross-correlation arithmetic between echo signal sequences constituted by echo signal values at different sampling points in the direction along the scan lines at said different time points, and finding a displacement in a direction along said group of curves substantially orthogonal to the scan lines by performing cross-correlation arithmetic between echo signal sequences constituted by echo signal values at different sampling points along the curves substantially orthogonal to the scan lines at said different time points.

9. An ultrasonic diagnostic device comprising:

an ultrasonic probe constituted by a group of ultrasonic transducer elements arranged in at least one direction;

a beam forming unit for forming acoustic field sensitivity modulated in a direction substantially orthogonal to a group of scan lines in a subject by focusing an ultrasonic wave on a sequence of sampling points existing along the group of scan lines, and applying delay and apodization on a transmission/reception signal of each of the ultrasonic transducer elements; and a detecting unit for detecting displacements in at least two directions at each of the sampling points by performing arithmetic operations on reception signals for the sampling point at different time points, wherein said detecting unit detects displacements at the sampling point in a first and second respective directions, that are respectively tangential to a scan line that passes through the sampling point and to a curve that passes through the sampling point, wherein the curve belongs to a family of curves substantially orthogonal to the scan lines, and wherein the first and second directions are respectively tangential to the scan line and the curve at the sampling point, wherein the group of curves is in the subject, each of the curves being defined by a sequence of points for which a total of times taken for ultrasonic pulses to reach the sequence of points from two fixed points on the ultrasonic probe is substantially the same.

10. An ultrasonic diagnostic system comprising:

an ultrasonic probe having a group of ultrasonic transducer elements arranged in at least one direction;

a beam forming unit for forming acoustic field sensitivity modulated in a direction substantially orthogonal to each scan line of a group of scan lines in a subject by focusing an ultrasonic wave on a sequence of sampling points existing along the group of scan lines, and applying delay and apodization to a transmission/reception signal of each of the ultrasonic transducer elements; and a detecting unit for detecting displacements in at least two directions at each of the sampling points by arithmetic between reception signals for the sampling point at different time points, wherein said detecting unit detects displacements at the sampling point in a first direction along the scan line that passes through the sampling point, and in a second direction tangential to a curve that passes through the sampling point, wherein the second direction is tangential to the curve at the sampling point, and wherein the curve belongs to a group of curves substantially orthogonal to the scan lines, wherein said group of scan lines is a group of straight lines each radially extending through one point fixed to said ultrasonic probe, and said group of curves substantially orthogonal is a group of concentric circles each having said one point as a common middle point.

11. An ultrasonic diagnostic system comprising:

an ultrasonic probe having a group of ultrasonic transducer elements arranged in at least one direction;

a beam forming unit for forming acoustic field sensitivity modulated in a direction substantially orthogonal to each scan line of a group of scan lines in a subject by focusing an ultrasonic wave on a sequence of sampling points existing along at least a portion of each scan line of the group of scan lines, and applying delay and apodization to a transmission/reception signal of each of the ultrasonic transducer elements; and a detecting unit for detecting displacements in at least two directions at each of the sampling points by arithmetic between reception signals for the sampling point at different time points, wherein said detecting unit detects displacements at the sampling point in a first direction tangential to or collinear with the scan line at the sampling point, and in a second direction tangential to a curve at the sampling point, wherein the sampling points are defined at intersections of scan lines and curves that are substantially orthogonal to the scan lines, wherein a group of the curves substantially orthogonal to the group of scan lines is a group of curves in the subject, wherein each of the curves is defined by a sequence of points for which a total of times taken for ultrasonic pulses to reach the sequence of points from two fixed points on the ultrasonic probe is substantially the same, and wherein said group of scan lines are hyperbolas or asymptotes of hyperbolas, the hyperbolas having, as common focal points, the two fixed points on said ultrasonic probe.

* * * * *